United States Patent
Nagano et al.

(10) Patent No.: US 12,234,508 B2
(45) Date of Patent: Feb. 25, 2025

(54) DETECTION METHOD USING KIT FOR DETECTING PLURALITY OF TARGET NUCLEIC ACIDS

(71) Applicant: MIZUHO MEDY CO., LTD., Saga (JP)

(72) Inventors: Takashi Nagano, Saga (JP); Koichi Ebisu, Saga (JP); Kenji Narahara, Saga (JP); Kazuhiro Ichimaru, Saga (JP)

(73) Assignee: MIZUHO MEDY CO., LTD., Saga (JP)

( * ) Notice: Subject to any disclaimer, the term of this patent is extended or adjusted under 35 U.S.C. 154(b) by 990 days.

(21) Appl. No.: 17/276,654

(22) PCT Filed: Aug. 29, 2019

(86) PCT No.: PCT/JP2019/033917
§ 371 (c)(1),
(2) Date: Mar. 16, 2021

(87) PCT Pub. No.: WO2020/059458
PCT Pub. Date: Mar. 26, 2020

(65) Prior Publication Data
US 2022/0042071 A1 Feb. 10, 2022

(30) Foreign Application Priority Data
Sep. 18, 2018 (JP) .................................. 2018-173434

(51) Int. Cl.
*C12Q 1/686* (2018.01)
*C12N 9/22* (2006.01)
(Continued)

(52) U.S. Cl.
CPC ............... *C12Q 1/686* (2013.01); *C12N 9/22* (2013.01); *C12Q 1/6818* (2013.01); *G16B 40/10* (2019.02)

(58) Field of Classification Search
CPC .................. C12Q 1/686; C12Q 1/6818; C12Q 2527/107; C12Q 2537/143;
(Continued)

(56) References Cited

U.S. PATENT DOCUMENTS

2001/0000175 A1  4/2001  Kurane et al.
2002/0058258 A1  5/2002  Wittwer et al.
(Continued)

FOREIGN PATENT DOCUMENTS

CA  2983428 C  * 12/2021  ............... C12Q 1/68
CN  101168776  4/2008
(Continued)

OTHER PUBLICATIONS

International Search Report, issued Oct. 29, 2019 in corresponding International Patent Application No. PCT/JP2019/033917, with English language translation.
(Continued)

*Primary Examiner* — Jesse P Frumkin
(74) *Attorney, Agent, or Firm* — Wenderoth, Lind & Ponack, L.L.P.

(57) ABSTRACT

The present invention provides a method for detecting multiple target nucleic acids, the method making it possible to amplify a plurality of genes using one reaction vessel containing therein one type of reaction solution and further using a single label. Computation is performed in accordance with the following formulas for every specific cycle and/or every cycle during amplification reaction using a kit for detecting the multiple target nucleic acids. (Formula 1): $f1[n]=fhyb.1[n]/fden.1[n]$, (Formula 1'): $f2[n]=fhyb.2[n]/$
(Continued)

fden.2[n], (Formula 2): Fr[n]=(a−f2 [n])/(a−f1 [n]).fhyb.1 [n]: Fluorescence intensity value in elongation step of first target nucleic acid detecting step. The same hereinafter.

6 Claims, 28 Drawing Sheets

Specification includes a Sequence Listing.

(51) Int. Cl.
*C12Q 1/6818* (2018.01)
*G16B 40/10* (2019.01)

(58) Field of Classification Search
CPC ........ C12Q 2537/165; C12Q 2563/107; C12N 9/22; G16B 40/10
See application file for complete search history.

(56) References Cited

U.S. PATENT DOCUMENTS

| | | | |
|---|---|---|---|
| 2006/0047443 | A1 | 3/2006 | Namkoong et al. |
| 2009/0155891 | A1 | 6/2009 | Tamaoki et al. |
| 2012/0202203 | A1* | 8/2012 | Reis, Jr. ............... C12Q 1/689 435/6.11 |
| 2014/0038195 | A1* | 2/2014 | Malik ................. C12Q 1/6851 435/6.12 |
| 2018/0155764 | A1* | 6/2018 | Nagano ................ C12Q 1/6816 |
| 2021/0238653 | A1* | 8/2021 | Nagano ................ C12Q 1/6816 |
| 2021/0292817 | A1* | 9/2021 | Rajagopal ........... C12Q 1/6816 |

FOREIGN PATENT DOCUMENTS

| | | |
|---|---|---|
| EP | 3 305 912 | 4/2018 |
| JP | 2002-136300 | 5/2002 |
| JP | 2004-000203 | 1/2004 |
| JP | 2004-305219 | 11/2004 |
| JP | 2006-68011 | 3/2006 |
| JP | 2007-236219 | 9/2007 |
| JP | 2008-173127 | 7/2008 |
| JP | 2012-513215 | 6/2012 |
| WO | WO-2015147382 A1 * | 10/2015 ........... C12Q 1/6827 |
| WO | 2016/194552 | 12/2016 |
| WO | WO-2016194552 A1 * | 12/2016 ............... C12Q 1/68 |

OTHER PUBLICATIONS

Extended European Search Report issued on May 13, 2022 in corresponding European Patent Application No. 19863731.6.

* cited by examiner

SEQUENCE LISTING

```
<160> NUMBER OF SEQ ID NOS: 9

<210> SEQ ID NO 1
<211> LENGTH: 26
<212> TYPE: DNA
<213> ORGANISM: Chlamydia trachomatis

<400> SEQUENCE: 1
ttgcagcttg tagtcctgct tgagag                                          26

<210> SEQ ID NO 2
<211> LENGTH: 35
<212> TYPE: DNA
<213> ORGANISM: Chlamydia trachomatis

<400> SEQUENCE: 2
gcactttcta caagagtaca tcggtcaacg aagag                                35

<210> SEQ ID NO 3
<211> LENGTH: 24
<212> TYPE: DNA
<213> ORGANISM: Neisseria gonorrhoeae

<400> SEQUENCE: 3
tcctcagggc gtggttgaac tggc                                            24

<210> SEQ ID NO 4
<211> LENGTH: 29
<212> TYPE: DNA
<213> ORGANISM: Neisseria gonorrhoeae

<400> SEQUENCE: 4
```

-continued

```
ccctcgaat tttgcttagt cggtcatgg                                  29

<210> SEQ ID NO 5
<211> LENGTH: 26
<212> TYPE: DNA
<213> ORGANISM: Chlamydia trachomatis

<400> SEQUENCE: 5
tgcgggcgat ttgccttaac cccacc                                    26

<210> SEQ ID NO 6
<211> LENGTH: 25
<212> TYPE: DNA
<213> ORGANISM: Neisseria gonorrhoeae

<400> SEQUENCE: 6
cattttaccg attttttcag acaac                                     25

<210> SEQ ID NO 7
<211> LENGTH: 29
<212> TYPE: DNA
<213> ORGANISM: Mycoplasma pneumoniae

<400> SEQUENCE: 7
ctcggtgaaa tccaggtacg ggtgaagac                                 29

<210> SEQ ID NO 8
<211> LENGTH: 40
<212> TYPE: DNA
<213> ORGANISM: Mycoplasma pneumoniae

<400> SEQUENCE: 8
gcatcgattg ctcctaccta ttctctacat gataatgtcc                     40

<210> SEQ ID NO 9
<211> LENGTH: 25
<212> TYPE: DNA
<213> ORGANISM: Mycoplasma pneumoniae

<400> SEQUENCE: 9
acggaaagac cccgtgaagc tttac                                     25
```

DETECTION METHOD USING KIT FOR DETECTING PLURALITY OF TARGET NUCLEIC ACIDS

BACKGROUND OF THE INVENTION

1. Field of the Invention

The present invention relates to a detection method using a kit for detecting multiple target nucleic acids, the kit improving the PCR method and further measuring the multiple target nucleic acids.

2. Description of the Related Art

In genetic screening, it is necessary to measure multiple target nucleic acids in many cases. For example, the multiple target nucleic acids may be: a first pair of influenza type A and influenza type B; a second pair of influenza and RSV/human metapneumovirus; a third pair of Chlamydia and *Nisseria gonorrhoeae*, which may cause sexually transmitted diseases; a fourth pair of *Mycoplasma* and resistance factor thereof; and so on.

Regarding the multiple target nucleic acids in some pairs of the above, the conditions of patients are similar to each other and also infection of the same expands simultaneously. So, it is conceivable to distinguish the multiple target nucleic acids from each other to make a diagnosis, thereby deciding on a policy of treatment. Considering the resistance factor is effective for selecting/judging medication for thereto, or the like.

As for only one measurement item, it is also helpful to set up internal control composition as a means for confirming whether or not the measurement itself has been well done.

This is performed by: beforehand preparing a nucleic acid sequence to be amplified, the sequence not concerning a target gene of a detection object; and enabling to confirm whether or not the reaction has been well processed in spite of the existence or non-existence of the target nucleic gene.

In this way, whether or not the reagent and the device for the measurement have acted effectively can be checked within a measurement system.

As mentioned above, in order to detect the multiple target nucleic acids, a first process of performing independent measurement for each of the multiple target nucleic acids, respectively, and a second process of distinguishing the multiple target nucleic acids from each other by means of different pilot dyes or the like, respectively may be conceived.

Alternatively, it is also possible to carry out the melting curve analysis method after having simultaneously processed amplification reaction. In this method after the amplification reaction, temperature is gradually increased/decreased to make distinction and judgment with respect to the multiple target nucleic acids based on both of first temperature wherein a change rate of fluorescent signals shows a peak and second temperature wherein the target numeric acid is melt (that is, a thermal melting curve analysis method).

The first process of performing the independent measurement requires long time and high costs. The second process of distinguishing different labeling substances from each other costs too much because the second process needs not only preparing plural kinds of labeled reagents but also complicated wavelength-setting in an analyzer.

A case by means of the thermal melting curve analysis method costs less than the above. However, since the temperature must be gradually changed, it is necessary to take about 5 to 10 minutes for changing the temperature in order to conduct precise analysis.

Reference 1 (Japanese application Laid-open No. 2002-136300) discloses: a method comprising: preparing a plurality of reaction vessels containing different reaction solution from each other; and performing amplification and detection with the plurality of reaction vessels, respectively.

So, reagent preparation and dispensing operations must be conducted for every item of the plurality of reaction vessels. There is a problem that the method requires a long time.

Reference 2 (Japanese application Laid-open No. 2004-203) discloses a method comprising simultaneously amplifying multiple genes by means of one reaction vessel containing one kind of reaction solution.

Distinction is carried out by using different pilot dyes for each of the multiple genes. Namely, a plurality of colors are used.

In this way a plurality of optical systems installed in an analyzer are needed as many as the used pilot dyes (the used colors). In other words, the analyzer costs too much. This is a serious problem.

Reference 3 (Japanese application Laid-open No. 2008-173127) discloses a method comprising simultaneously amplifying multiple genes by means of one reaction vessel containing one kind of reaction solution.

Dissociation temperature of PCR products and labeled probes should be changed for every gene. After amplification, while temperature is gradually increased from a lower temperature side to a higher temperature side, dissociation curve analysis, which is a synonym of "thermal melting curve analysis", of monitoring fluorescence values is carried out. Distinction is carried out by monitoring existence or non-existence of a peak depending on base sequence at the respective dissociation temperature.

If the temperature is changed speedily upon the melting curve analysis, it becomes difficult to identify melting temperature for each gene. Accordingly, there is a problem that extra time of about 5 to 10 minutes after PCR is required.

Reference 4 (Japanese unexamined patent application publication <Translation of PCT application> No. 2012-513215) discloses a method comprising simultaneously amplifying multiple genes by means of one reaction vessel.

Dissociation temperature of PCR products and melting temperature of primers are changed for every gene. Distinction is carried out by monitoring fluorescence at the respective melting temperature.

In a common PCR profile, one cycle includes: a denaturation step; and an annealing and elongation step. In Reference 4, the melting temperature of PCR products is changed for every gene. Accordingly, too many conditions should be taken into consideration, design of the profile is also difficult, and time for measurement must be too long.

Furthermore, there is another problem that temperature must be drastically changed to task the device.

As mentioned above, a common problem upon simultaneously amplifying multiple genes by means of one reaction vessel containing one kind of reaction solution is that fluorescent signals interfere with each other to make distinction there-between impossible caused by base sequences of target genes and/or probes.

LIST OF CITED REFERENCES

Reference 1: Japanese application Laid-open No. 2002-136300;
Reference 2: Japanese application Laid-open No. 2004-203;

Reference 3: Japanese application Laid-open No. 2008-173127;
Reference 4: Japanese unexamined patent application publication <Translation of PCT application No. 2012-513215;
Reference 5: WO 2016/194552; and
Reference 6: Japanese registered patent No. 4724380.

OBJECTS AND SUMMARY OF THE INVENTION

In view of the above, an object of the present invention is to provide a kit for detecting multiple target nucleic acids capable of simultaneously amplifying and detecting multiple genes by means of one reaction vessel containing one kind of reaction solution and one label and a detection method using the same.

A first aspect of the present invention provides a detection method, comprising: performing calculation in accordance with a plurality of formulas for every specific cycle and/or every cycle during amplification reaction while using a kit for detecting multiple target nucleic acids including a first target nucleic acid and a second target nucleic acid differing from each other.

Herein, the plurality of formulas include:

$$f1[n]=fhyb.1[n]/fden.1[n];$$ (Formula 1):

$$f2[n]=fhyb.2[n]/fden.2[n]; \text{ and}$$ (Formula 1'):

$$Fr[n]=(a-f2[n])/(a-f1[n]),$$ (Formula 2):

wherein: f1[n] is a first fluorescence intensity value calculated in accordance with the Formula 1 in a first target nucleic acid detection step in an n-th cycle; fhyb.1[n] is a second fluorescence intensity value in an elongation step of the first target nucleic acid detection step in the n-th cycle; fden.1[n] is a third fluorescence intensity value in a denaturation step of the first target nucleic acid detection step in the n-th cycle; f2[n] is a fourth fluorescence intensity value calculated in accordance with the Formula 1' in a first and second target nucleic acid detection step in the n-th cycle; fhyb.2[n] is a fifth fluorescence intensity value in an elongation step of the first and second target nucleic acid detection step in the n-th cycle; fden.2[n] is a sixth fluorescence intensity value in a denaturation step of the first and second target nucleic acid detection step in the n-th cycle; "a" is a fixed number making Fr not to be zero or less; and Fr [n] is a first calculated value for detecting the second target nucleic acid.

Herein, "one cycle" according to the present invention means a continuous pair of a first and second target nucleic acid detection step and a first target nucleic acid detection step as shown in FIG. 2. It should be noted that the "one cycle" according to the present invention corresponds to two cycles in common PCR.

With respect to the kit for detecting the multiple target nucleic acids, temperature is set up as follows: that is, T0 is defined as denaturation temperature; T1 is defined as annealing temperature; T2 is defined as elongation temperature; and T3 is defined as second target detection temperature, T0 through T3 being set up such that a condition of T0>T2>=T1>T3 is satisfied.

For the kit for detecting the multiple target nucleic acids, solution is used; the solution being capable of containing the first target nucleic acid and the second target nucleic acid therein, at the denaturation temperature T0, first double-stranded hydrogen bond of the first target nucleic acid being cut off to be dissociate into first two single strands, second double-stranded hydrogen bond of the second target nucleic acid being cut off to be dissociate into second two single strands, respectively.

The solution contains therein: a first target's primer at the annealing temperature T1 specifically bonding with either of the first two single strands into which the first target nucleic acid has been dissociated; a second target's primer at the annealing temperature T1 specifically bonding with either of the second two single strands into which the second target nucleic acid has been dissociated; a first target's probe at the annealing temperature T1 specifically bonding with either of the first two single strands into which the first target nucleic acid has been dissociated, the first target's probe including a first labeling substance changing first fluorescent signals thereof when the first target's probe specifically bonds with either of the first two single strands; DNA polymerase; deoxyribonucleoside triphoshate at the elongation temperature T2 bonding by action of the DNA polymerase with both of the first two single strands into which the first target nucleic acid has been dissociated and the second two single strands into which the second target nucleic acid has been dissociated; a second target's probe at the annealing temperature T1 bonding with neither the first two single strands into which the first target nucleic acid has been dissociated nor the second two single strands into which the second target nucleic acid has been dissociated, the second target's probe at the second target detection temperature T3 bonding with the second two single strands into which the second target nucleic acid has been dissociated, the second target's probe including a second labeling substance changing second fluorescent signals thereof when the second target's probe specifically bonds with either of the second two single strands.

Furthermore herein, the first labeling substance and the second labeling substance are identical to each other so that the first fluorescent signals caused by the first labeling substance and the second fluorescent signals caused by the second labeling substance are also identical to each other.

In addition to the first aspect of the present invention, it is preferable that the detection method further comprises: performing further calculation in accordance with further formulas, wherein the further formulas include:

$$F1[n]=f1[n]/f1[X];$$ (Formula 3)

$$F2[n]=f2[n]/f2[X]; \text{ and}$$ (Formula 3')

$$Fr'[n]=(a-F2[n])/(a-F1[n]),$$ (Formula 2')

wherein: f1 [X] is a seventh fluorescence intensity value in an X cycle; the seventh fluorescence intensity f1[X] is stable in the X cycle; the multiple target nucleic acids have not been amplified yet until the X cycle; the seventh fluorescence intensity f1 [X] is used as a first criterion in change of fluorescence intensity values in the first target nucleic acid detection step; f2 [X] is an eighth fluorescence intensity value in the X cycle; the eighth fluorescence intensity f2[X] is stable; the multiple target nucleic acids have not been amplified yet until the X cycle; the eighth fluorescence intensity f2 [X] being used as a second criterion in change of fluorescence intensity values in the first and second target nucleic acid detection step; F1[n] is a first relative value in the n-th cycle when assuming a fluorescence intensity value obtained in accordance with the Formula 3 in the X cycle as "1"; F2[n] being a second relative value in n-th cycle when assuming a fluorescence intensity value obtained in accordance with the Formula 3' in the X cycle as "1"; and Fr' [n] is a second calculated value for detecting the second target nucleic acid.

A second aspect of the present invention provides a detection method, comprising: performing calculation in accordance with a plurality of formulas with respect to melting curve analysis while using a kit for detecting multiple target nucleic acids.

The plurality of formulas include:

$f$em.=$f$hyb.1m/$f$den.1m;  (Formula 4):

$f$2m=$f$hyb.2m/$f$den.2m; and  (Formula 4'):

Frm=(a-$f$2m)/(a-$f$1m),  (Formula 5):

wherein: f1m is a first fluorescence intensity value calculated with respect to a melting curve in accordance with the Formula 4 in a first target nucleic acid detection step; fhyb.1m is a second fluorescence intensity value at first probe for first target hybridization temperature with respect to the melting curve; fden.1m is a third fluorescence intensity value at first probe for first target dissociation temperature with respect to the melting curve; f2m is a fourth fluorescence intensity value calculated in accordance with the Formula 4' with respect to the melting curve in a first and second target nucleic acid detection step; fhyb.2m is a fifth fluorescence intensity value at second probe for second target hybridization temperature with respect to the melting curve; fden.2m is a sixth fluorescence intensity value at second probe for second target dissociation temperature with respect to the melting curve and being identical to fden.1m; "a" is a fixed number making Frm to not be zero or less; and Frm is a third calculated value for detecting the second target nucleic acid.

It is preferable that a pair of the first labeling substance and the second labeling substance is selected from a group consisting of: a Quenching probe, an Extinction probe, and a hydrolysis probe.

The fluorescent signals may be shown by at least one of: emitting light when annealing occurs; and quenching light when annealing occurs.

It is preferable that a pair of the first target nucleic acid and the second target nucleic acid is at least one of: a wild type sequence of a *Mycoplasma* 23S rRNA gene and a sequence with drug resistance variation of a *Mycoplasma* 23 S rRNA gene; and a Chlamydia endogeneous plasmid gene and a *Nisseria gonorrhoeae* cytosine methyltransferase CMT gene.

Needless to say, the present invention may be performed according to the intercalator method.

Effect of Invention

As mentioned above, according to the present invention, the multiple target nucleic acids can be detected by means of one kind of mixed-solution and one kind of labeling substance.

Since there is little restriction regarding design of probes identifying multiple target nucleic acids, measuring time and analysis time can be shortened, thereby providing excellent practical performance.

DETAILED DESCRIPTION OF THE PREFERRED EMBODIMENTS

As shown in FIG. 21, the present invention uses four kinds of temperature including: denaturation temperature T0 (95 Centigrade); annealing temperature T1 (70 Centigrade); elongation temperature T2 (72 Centigrade); and second target detection temperature T3 (55 Centigrade). The four kinds of temperature are set such that a condition that T0>T2>=T1>T3 is satisfied. Needless to say, the above temperature values are mere examples, and can be variously changed as mentioned later.

Herein, the multiple target nucleic acids are a first target nucleic acid and a second target nucleic acid. However if needed, a third target numeric acid or more can be added thereto by adding further setting such as third target detection temperature T4 (T3>T4), or the like.

Referring to FIG. 22, the components of the present invention will now be explained. First, in the present invention, it is assumed that a first target nucleic acid 10 and a second target nucleic acid 20 are targets to be detected. Hereinafter for the simplicity of explanation, only a case where both of the first target nucleic acid 10 and the second target nucleic acid 20 are contained in solution 2 within a vessel 1, that is, a case of positive and positive will be explained below. Details of the solution 2 will be mentioned later.

Needless to say, in another case where at least one target is negative, the solution 2 does not contain the at least one of the first target nucleic acid 10 and the second target nucleic acid 20. Therefore, fluorescent signals and amplification regarding the not contained target numeric acid will not be carried out in the following explanation.

As shown in FIG. 23 (a), when temperature of the solution 2 is increased to reach the denaturation temperature T0, hydrogen bonds of double strands of the first target nucleic acid 10 and the second target nucleic acid 20 are respectively cut off to be dissociated into respective first and second two single strands (from the first target nucleic acid 10 to a first single-strand 11 and a second single strand 12, from second target nucleic acid 20 to a first single-strand 21 and a second single strand 22).

As shown in FIG. 23 (b), the temperature is decreased from the denaturation temperature T0 to reach the annealing temperature T1, regarding the first target nucleic acid 10, an F first target's primer 13 specifically bonds with a complementary sequence of the first single strand 11, and an R first target's primer 14 specifically bonds with another complementary sequence of the second single strand 12. Furthermore, similar to the above, regarding the second target nucleic acid 20, an F second target's primer 23 specifically bonds with a complementary sequence of the first single strand 21, and an R second target's primer 24 specifically bonds with another complementary sequence of the second single strand 22.

At the annealing temperature T1 shown in FIG. 23 (b), the first target's probe 15 labeled by means of the first labeling substance 16 specifically bonds with a specific part of the first single strand 11 derived from the first target nucleic acid 10, thereby the first labeling substance 16 outputs first fluorescence signals. On the other hand, the annealing temperature T1 is higher than the second target detection temperature T3. For this reason, the second target's probe 25 labeled by means of the second labeling substance 26 does not bond with the first single strand 21 derived from the second target nucleic acid 20, thereby the second labeling substance 26 outputs no fluorescence signal at this time.

As shown in FIG. 23 (c), when the temperature is increased from the annealing temperature T1 to the elongation temperature T2, processes of the amplification reaction advance as follows. This is because the solution 2 contains an amount sufficient for repeating PCR cycles of DNA polymerase 30 and deoxyribonucleoside triphoshate 31.

Regarding the first target nucleic acid 10, from the F first target's primer 13 bonding with the first single strand 11, and from the R first target's primer 14 bonding with the second single strand 12, the deoxyribonucleoside triphoshate 31 bonds therewith to elongate, respectively.

Regarding the second target nucleic acid 20, from the F second target's primer 23 bonding with the first single strand 21, and from the R second target's primer 24 bonding with the second single strand 22, the deoxyribonucleoside triphoshate 31 bonds therewith to elongate, respectively.

As clear comparing FIG. 23 (d) with FIG. 22, upon the amplification reaction has been completed, both of the first target nucleic acid 10 and the second target nucleic acid 20 have been doubled.

Returning to a step shown in FIG. 23 (a) again, repeating the above steps of FIG. 23 (a) through FIG. 23 (d) enables to repeat changes of fluorescent signals and the amplification reaction by means of the first labeling substance 16.

Next referring to FIG. 24, a case where the temperature is decreased from the denaturation temperature T0 to the second target detection temperature T3 will now be explained.

As shown in FIG. 24 (a), at the denaturation temperature T0, the situation is the same as that of FIG. 23 (a). However, upon the temperature is decreased to reach the second target temperature detection temperature T3, the situation is as shown in FIG. 24 (b) differing from that of FIG. 23 (b).

Namely, as shown in FIG. 24 (b), the first target's probe 15 labeled by the first labeling substance 16 specifically bonds with a specific part of the first single strand 11 derived from the first target nucleic acid 10, and the fluorescent signals of the first labeling substance 16 change. This is the same as that of FIG. 23 (b). However, the temperature is the second target detection temperature T3. Accordingly, also the second target's probe 25 labeled by the second labeling substance 26 bonds with the first single strand 21 derived from the second target nucleic acid 20, and the fluorescent signals of the second labeling substance 26 also change. Herein, it is preferable that the first labeling substance 16 and the second labeling substance 26 are identical to each other.

Since at the bonding temperature T1 of the first target's probe 15 the second target's probe 25 does not bond, capturing the change of the fluorescent signals of the first labeling substance 16 enables to judge the existence/non-existence (positive/negative) of the first target nucleic acid 10.

In the present invention, the existence/non-existence (positive/negative) of the second target nucleic acid 20 is judged by capturing relative variation quantity between the change of the fluorescent signals of the first labeling substance 16 at the bonding temperature T1 and the change of the fluorescent signals caused by the second labeling substance 26 at the second target detection temperature T3.

In addition as clear from the above-mentioned, it may be understood that the multiple target nucleic acids can be respectively detected during a series of continuing steps by means of the reaction vessel containing one kind of reaction solution.

Hereinafter, Embodiments of detecting multiple nucleic acids by means of the QProbe (registered trademark) method, which is a representative example of Extinction Probes, will now be explained more concretely.

Necessary information for operation including: primer sequences; base sequences of the respective probes; and material of nucleic acid samples will be also shown.

Embodiment 1

<Detection of Chlamydia Endogeneous Plasmid Genes and Nisseria gonorrhoeae Cytosine Methyltransferase CMT Genes According to the QProbe Method>

Detection of *Chlamydia trachomatis* and *Neisseria gonorrhoea* is performed according to the QProbe method at the same time.

In Embodiment 1, pCT having a first target sequence of internal plasmid with respect to *Chlamydia trachomatis* and pNG having a second target sequence of cytosine methyltransferase with respect to of *Neisseria gonorrhoea* are applied to nucleic acid samples, respectively to perform PCR thereon. After that, judgment is performed by means of two kinds of QProbes corresponding to the first and second target sequences, respectively.

<Material and Steps>

A pair of primers used for the PCR method in Embodiment 1 is as shown in Table 1.

TABLE 1

| Name | Sequence(5'→3') |
| --- | --- |
| Chl 42F | TTGCAGCTTGTAGTCCTGCTTGAGAG<br>SEQ No. 1 |
| Chl 39R | GCACTTTCTACAAGAGTACATCGGTCAACGAAGAG<br>SEQ NO. 2 |
| NG F11 | TCCTCAGGGCGTGGTTGAACTGGC<br>SEQ NO. 3 |
| NG R13 | CCCCTCGAATTTTGCTTAGTCGGTCATGG<br>SEQ No. 4 |

(Nucleic Acid Sample)

Nucleic acid samples used for the PCR method in Embodiment 1 are shown below.

(STD CT1)

*Chlamydia trachomatis* is a pathogenic organism of sexual organ Chlamydia disease. Gene fragments of common internal plasmid to *Chlamydia trachomatis* are artificially synthesized to be incorporated into a pMD20T vector. Production of the plasmid DNA has been performed by requesting custom synthesis to the Takara Bio Inc.

(STD NG1)

*Neisseria gonorrhoeae* is a pathogenic origin of gonorrhea. Gene fragments of cytosine DNA methyltransferase (CMT) of *Neisseria gonorrhoea* are artificially synthesized to be incorporated into a pMD20T vector. Production of the plasmid DNA has been performed by requesting custom synthesis to the Takara Bio Inc.

(Preparation of Nucleic Acid Sample)

First length of the STD CT1 plasmid is 122 [bp], and second length of the STD NG1 plasmid is 137 [bp].

Based on the first and second length and the concentration [μg/□μl] of plasmid solution, the number of copies per 1 [11] has been calculated. After that, by means of TE buffer solution (10 [mM] Tris-HCl, 1.0 [mM] EDTA pH: 8.0), both of the STD CT1 plasmid and the STD NG1 plasmid has been diluted to be $4.4 \times 10^2$ [copies/□μl] or $1.1 \times 10^6$ [copies/□μl], respectively.

(Probe)

Information of the probes used for the PCR method in Embodiment 1 is as shown in Table 2.

TABLE 2

| Name | Sequence (5'→3') |
|---|---|
| CT QP1 | TGCGGGCGATTTGCCTTAACCCCACC SEQ No. 5 |
| NG QP5 | CATTTTACCGATTTTTTCAGACAAC SEQ No. 6 |

Based on a basic sequence of PCR products capable of being amplified by means of a pair of primers of the No. 1 sequence and the No. 2 sequence in Table 1, a first specific region of CT QP1 has been selected referring to Tm values calculated with a QProbe design support tool on the J-Bio21 Center home pages.

"CT QP1" is one QProbe specifically annealing the STD CT1 plasmid, and "NG QP5" is another QProbe specifically annealing the STD NG1 plasmid. As fluorescent dye for both of "CT QP1" and "NG QP5", "BODIPY FL" (registered trademark) has been used to label "C" at 3' ends, respectively. Production of the QProbes has been performed by requesting custom synthesis to the NIPPON STEEL & SUMIKIN Eco-Tech Corporation.

(Conditions of PCR and Fluorescence Measurement)

In Embodiment 1, among two kinds of target nucleic acids to be amplified within one vessel containing one kind of reaction liquid, a first Tm value for "STD CT1" that is the QProbe (CT QP1) specifically annealing the STD CT1 plasmid of the first target is set up to be higher than another Tm value for the primers to perform first detection during amplification reaction.

In addition, a second Tm value for "NG QP5" that is the QProbe specifically annealing the STD NG1 plasmid of the second target is set up to be lower than the first Tm value with respect to the QProbe (CT QP1).

In such conditions, fluorescence intensity is measured to perform judgment at: a first temperature where CT QP1 and STD CT1 are expected to hybridize to each other; and a second temperature which is lower than the first temperature, respectively.

Table 3 and Table 4 show composition of the PCR reaction solution and the reaction conditions respectively, and FIG. 1 is a graph showing change of temperature of the mixed solution related thereto.

TABLE 3

| Solution composition | Final concentration |
|---|---|
| Solution composition | |
| MilliQ water(™) | — |
| PCR buffer | ×1 |
| dNTP Mix | 150 μM |
| Chl 42F | 0.135 μM |
| Chl 39R | 0.405 μM |
| NG F11 | 0.200 μM |
| NG R13 | 0.600 μM |
| CT QP1 | 0.080 μM |
| NG QP5 | 0.080 μM |
| KOD exo (−) DNA Polymerase | 0.0125 U/μM |
| target NA | |

Prepared to be μL

TABLE 4

| Reaction stage | Temperature (° C.) | | Time (Sec) |
|---|---|---|---|
| Early denaturation | 95 | T0 | 120 |
| Amp reaction (1-23 cycle) | | | |
| Detecting first and | 95 | T0 | 10 (Measure FL) |
| second target | 60 | T3 | 10 (Measure FL) |
| Detecting first target | 95 | T0 | 10 (Measure FL) |
| | 67 | T2 => T1 | 10 (Measure FL) |

A PCR device in the name of "Smart Gene" (registered trademark in Japan) manufactured by the Mizuho Medy Co., Ltd. has been used for the PCR and the fluorescence measurement.

Based on the center wavelength of 525 [nm], excitation wavelength and fluorescent wavelength upon fluorescence measurement have been set up, respectively.

Fluorescence values have been measured at a first step for detecting the first target nucleic acid (95 Centigrade and 67 Centigrade) and a second step for detecting the first target nucleic acid, and second target nucleic acid (95 Centigrade and 60 Centigrade) during amplification reaction.

FIG. 2 shows fluorescent measurement conditions during the amplification reaction related thereto.

(How to Handle Data)

As analysis by means of the QProbes, correction calculation has been performed on obtained raw data as follows, referring to a method disclosed in Reference 6 (Japanese registered patent No. 4724380).

For every cycle of the amplification reaction, a fluorescence intensity value f1[n] in the first target detection step in n-th cycle is calculated by means of the Formula 1.

As first values for this calculation, a fluorescence intensity value fhyb.1[n] at 67 Centigrade in the first target detection step and an intensity value fden.1[n] at 95 Centigrade in the first target detection step are used.

Similar to the above, for every cycle during the amplification reaction, a fluorescence intensity value f2[n] in the first and second target detection step in n-th cycle is calculated by means of the Formula 1'.

As second values for this calculation, a fluorescence intensity value fhyb.2[n] at 60 Centigrade in the first and second target detection step and an intensity value fden.2[n] at 95 Centigrade in the first and second target detection step are used.

Next, for every cycle during the amplification reaction, a number of "10" is substituted for X in the Formula 3, and a fluorescence intensity value f1[10] in tenth cycle obtained according to the Formula 1 is assumed to be a number of "1". And then, a relative value F1 [n] in n-th cycle is calculated.

In addition, a number of "10" is substituted for X in the Formula 3', and a fluorescence intensity value f2[10] in tenth cycle obtained according to the Formula 1' is assumed to be a number of "1". And then, a relative value F2 [n] in n-th cycle is calculated.

A value of F1 [23], which is a value of F1 [n] in the final cycle of the amplification reaction, is used for judgment of Chlamydia which is the first target nucleic acid.

Furthermore, a number of "1.1" is substituted for the constant "a", and then the value of Fr[n] is calculated. In addition, a number of "1.05" is substituted for the constant "a", and then the value of Fr' [n] is calculated.

Values of Fr[23] and Fr' [23], which are values of Fr' [n] and Fr' [23] in the final cycle of the amplification reaction, are used for judgment of *Nisseria gonorrhoeae* which is the second target nucleic acid. FIG. 3 shows the flowchart with respect to this judgment related thereto.

A Tm value for the sequence of CT QP1 is set up to be 73.4 Centigrade, and a TM value for the sequence of NG QP5 is set up to be 57.6 Centigrade.

For this reason, at the first target detection step at 95 Centigrade and 67 Centigrade during the amplification reaction, it is supposed that only CT QP1 anneals to the first target nucleic acid.

On the other hand, in the first target and the second target detection step at 95 Centigrade and 60 Centigrade, it is supposed that not only CT QP1 anneals to the first target nucleic acid but also NG QP5 anneals to the second target nucleic acid.

In such conditions, referring to measurement values in the first target and the second target detection step, it is supposed to detect that fluorescence caused by both of CT QP1 and NG QP5 are quenched at the same time.

In view of an amplification curve of the negative reference (sample wherein TE buffer solution is added thereto instead of DNA), quenching light has not been observed until 23-rd cycle when the PCR ends. FIG. 4 shows the amplification curve related thereto.

With respect to STD CT1 of $4.4 \times 10^2$ [copies/tube], quenching light with respect to both of the values of F1[n] and F2 [n] caused by annealing of CT QP1 has been observed from near 20th cycles on the amplification curve. FIG. 5 shows the amplification curve related thereto.

With respect to STD CT1 of $1.1 \times 10^6$ [copies/tube], quenching light with respect to both of the values of F1[n] and F2 [n] caused by annealing of CT QP1 has been observed from near 15th cycle on the amplification curve. FIG. 6 shows the amplification curve related thereto.

With respect to STD CT1 of $4.4 \times 10^2$ [copies/tube], quenching light with respect to the value of F2 [n] caused by annealing of NG QP5 has been observed from near 22nd cycles on the amplification curve. However, quenching light with respect to the value of F1 [n] has not been observed until 23-th cycle when the PCR ends. FIG. 7 shows the amplification curve related thereto.

With respect to STD CT1 of $1.1 \times 10^6$ [copies/tube], quenching light with respect to the value of F2 [n] caused by annealing of NG QP5 has been observed from near 16th cycles on the amplification curve. However, quenching light with respect to the value of F1 [n] has not been observed until 23-th cycle when the PCR ends. FIG. 8 shows the amplification curve related thereto.

(Judgment of First Target Nucleic Acid)

The value of F1 [23] is used to judge whether or not STD CT1 of the first target nucleic acid exists.

Threshold 1 of 0.9873 (N=5) is used as a threshold for the judgment. Herein, Threshold 1=the average value of F1 [23]−3*the standard deviation of F1 [23], both of which being related to the negative reference.

When the value of F1[23] is less than Threshold 1, it is judged to be first target nucleic acid positive (Chlamydia positive).

Since the value of 1.0028, which is the value of F1 [23] with respect to the negative reference, is greater than Threshold 1, it is judged that the negative reference is negative (Chlamydia negative).

Since both of the value of 0.9255 (the value of F1[23] with respect to STD CT1 of $4.4 \times 10^2$ [copies/tube]) and the value of 0.8106 (the value of F1[23] with respect to STD CT1 of $1.1 \times 10^6$ [copies/tube]) are less than Threshold 1, they are judged to be Chlamydia positive.

Since both of the value 1.0071 (the value of F1[23] with respect to STD NG1 of $4.4 \times 10^2$ [copies/tube]) and the value of 0.9999 (the value of F1[23] with respect to STD NG1 of $1.1 \times 10^6$ [copies/tube]) are greater than Threshold 1, they are judged to be Chlamydia negative.

(Judgment of Second Target Nucleic Acid)

Next, judgment of the second target nucleic acid according to the present invention will now be performed using the values of Fr [23] and Fr' [23] which are the values of Fr [n] and Fr' [n] in the 23rd cycle.

Threshold 2 of 1.2312 (N=4) is used as a threshold for the judgment. Herein, Threshold 2=the average value of Fr [23]−3*the standard deviation of Fr [23], both of which being related to the negative reference (N=2) and eight examples of STD CT1 (N=2) of $1.1 \times 10^6$ [copies/tube] and STD CT1 (N=4) of $4.4 \times 10^2$ [copies/tube].

Threshold 2' of 1.1278 is also used. Herein, Threshold 2'=the average value of calculated value Fr' [23]− 3*the standard deviation of calculated value Fr' [23].

If at least one of a first condition where the value of Fr[23] is greater than Threshold 2 and a second condition where the value of Fr'[23] is greater than Threshold 2' is fulfilled, it is judged to be second target nucleic acid positive (*Nisseria gonorrhoeae* positive).

Since the value of 0.8633 (the value of Fr[23] with respect to STD CT1 of $4.4 \times 10^2$ [copies/tube]) is less than Threshold 2, the value of 1.1020 (the value of Fr' [23] with respect to STD CT1 of $1.1 \times 10^6$ [copies/tube]) is less than Threshold 2', and the value of 1.0664 of Fr'[23] is less than Threshold 2', they are judged to be *Nisseria gonorrhoeae* negative, respectively.

Since the value of 1.3472 (the value of Fr[23] with respect to STD NG1 of $4.4 \times 10^2$ [copies/tube]) is greater than Threshold 2, the value of 2.2578 (the value of Fr[23] with respect to STD NG1 of $1.1 \times 10^2$ [copies/tube]) is greater than Threshold 2, and the value of 3.0221 of Fr'[23] is greater than Threshold 2', they are judged to be *Nisseria gonorrhoeae* positive.

It is suggested that the value of Fr [23] becomes to be a greater value separated from Threshold 2 as concentration of the second target nucleic acid is higher.

Comparative Example 1

Utilizing the judgment method disclosed in Reference 5 by means of data obtained in Embodiment 1, judgment with respect to the second target nucleic acid will now be performed according to the following formula.

$$Fs[23]=F2[23]-F1[23] \tag{Formula 6}$$

A calculated value Fs [23] is used for judgment with respect to STD NG1, which is the second target nucleic acid.

Threshold 3 of −0.0295 is used as a threshold for judging the second target nucleic acid. Herein, Threshold 3=the average value of Fs [23]−3*the standard deviation of Fs [23], both of which being related to STD CT1 (N=6) of $1.1 \times 10^6$ [copies/tube].

When the value of Fs[23] is less than Threshold 3, it is judged to be second target nucleic acid positive (*Nisseria gonorrhoeae* positive).

Since the value of −0.0009, which is the calculated value Fs[23] with respect to the negative reference, is greater than Threshold 3, it is judged that the negative reference is negative (*Nisseria gonorrhoeae* negative).

Since the value of 0.0071 (calculated value Fs[23] with respect to STD CT1 of $4.4 \times 10^2$ [copies/tube]) is greater than Threshold 3, the value of −0.0120 (calculated value Fs[23]

with respect to STD NG1 of $4.4\times10^2$ [copies/tube]) is greater than Threshold 3, and the value of −0.0120 (calculated value Fs[23] with respect to STD NG1 of $4.4\times10^2$ [copies/tube]) is greater than Threshold 3, they are judged to be *Nisseria gonorrhoeae* negative, respectively.

Since the value of −0.1014 (calculated value Fs[23] with respect to STD NG1 of $1.1\times10^6$ [copies/tube]) is less than Threshold 3, it is judged to be *Nisseria gonorrhoeae* positive.

Table 5 shows: the relative fluorescence value F1[23] in 23rd cycle; the results of Chlamydia judgment; and the judgment results in Comparative Example 1 and Embodiment 1.

As mentioned above according to the conventional judgment method for the second target, it is revealed that distinguishing low concentration *Nisseria gonorrhoeae* is impossible.

This is because it is impossible to discriminate between a first change amount of F1 [23] caused by high concentration STD CT1 and a second change amount of F 1 [23] caused by low concentration STD NG1 according to the prior art.

On the contrary, according to the present invention, it is revealed that it is possible to simultaneously amplify and distinguish multiple genes by means of one reaction vessel containing one kind of reaction solution by means of one kind of labels without being influenced by the concentration of the first target nucleic acid.

As the above samples, the followings are used, including:
a first sample 1 containing STD CT1 and STD NG1 both in low concentration;
a second sample 2 containing STD CT1 in high concentration and STD NG1 in low concentration; and
a third sample 3 containing STD CT1 in low concentration and STD NG1 in high concentration.

With respect to the sample 1, on the amplification curves both of the values of F1[n] and F2 [n], quenching light is observed from near 21-th cycle. FIG. 9 shows the amplification curve related thereto.

With respect to the sample 2, on the amplification curves both of the values of F1[n] and F2 [n], quenching light is observed from near 15-th cycle. FIG. 10 shows the amplification curve related thereto.

With respect to the sample 1, on the amplification curve of the value of F1[n], quenching light is observed from near 20-th cycle, and on the amplification curve of the value of F2[n], quenching light is observed from near 16-th cycle. FIG. 11 shows the amplification curve related thereto.

(Judgment of First Target Nucleic Acid)

The value of F1 [23] is used to judge whether or not STD CT1 of the first target nucleic acid exists.

Threshold 1 of 0.9873 (N=5) in Embodiment 1 is used as a threshold for the judgment.

The values of F23[1] with respect to the first, second, and third samples 1, 2, and 3 are 0.9414, 0.8174, and 0.9328, respectively. Since all of these values are less than Threshold

TABLE 5

| DNA | Conc. (copies/tube) | Detecting first target | | Detecting first and second target | | | | | |
|---|---|---|---|---|---|---|---|---|---|
| | | | | C.E.1 | | Emb.1 | | | |
| | | F1 [23] | Chlam. | Fs [23] | N.G. | Fr [23] | N.G. | Fr' [23] | N.G. |
| N Ref | 0 | 1.0028 | − | −0.0009 | − | 1.1543 | − | 1.0196 | − |
| STD CT1 | 4.4 × 10^2 | 0.9255 | + | 0.0071 | − | 0.8633 | − | 0.9433 | − |
| STD CT1 | 1.1 × 10^6 | 0.8106 | + | −0.0159 | − | 1.1020 | − | 1.0664 | − |
| STD NG1 | 4.4 × 10^2 | 1.0071 | − | −0.0120 | − | 1.3472 | + | 1.2803 | + |
| STD NG1 | 1.1 × 10^6 | 0.9999 | − | −0.1014 | + | 2.2578 | + | 3.0221 | + |

−: Negative
+: Positive

Embodiment 2

<Simultaneous Detection of Multiple Targets According to QProbe Method>

When a patient is infected with *Chlamydia trachomatis* and *Neisseria gonorrhoea* in a mixed mode, only one of them presenting a stronger symptom may be diagnosed, and the other of them may be missed in some cases.

Effective medicines for *Chlamydia trachomatis* and *Neisseria gonorrhoea* differ from each other. Accordingly, it may be highly helpful clinically to distinguish the mixed infections by means of genetic screening.

Upon simultaneously amplifying and detecting multiple genes by means of one reaction vessel containing one kind of reaction solution by means of one kind of labels, fluorescence change caused by the respective labeling probes may interfere with each other. For this reason, it may be said that such distinction between these mixed infections has comparatively high difficulty.

In Embodiment 2, while using the materials and the methods in Embodiment 1, *Chlamydia trachomatis* positive and *Neisseria gonorrhoea* positive samples will now be measured to be distinguished there-between.

1, all of them are judged to be first target nucleic acid positive (Chlamydia positive).

(Judgment of Second Target Nucleic Acid)

Next, by means of the same procedures as Embodiment 1, judgment according to the present invention will now be performed.

The values of Fr' [23] with respect to the first, second, and third samples 1, 2, and 3 are 1.1378, 1.1364, and 1.8587, respectively. Since all of these values are greater than Threshold 2' in Embodiment 1, all of them are judged to be *Nisseria gonorrhoeae* positive.

Comparative Example 2

By means of the same procedures as Comparative Example 1, judgment with respect to the second target nucleic acid will now be performed as follows.

Since the value of Fs [23] with respect to the first sample 1 is −0.0150 which is greater than Threshold 3 (−0.0295) in Embodiment 1, the first sample 1 is judged to be *Nisseria gonorrhoeae* negative.

Since the value of Fs [23] with respect to the second sample 2 is −0.0317 and the value of Fs [23] with respect to the third sample 3 is −0.1006 each of which is less than Threshold 3, each of the second sample 2 and the third sample 3 is judged to be *Nisseria gonorrhoeae* positive.

Table 6 shows: the relative fluorescence value F1[23] in 23rd cycle; the results of Chlamydia judgment; and the judgment results in Comparative Example 2 and Embodiment 2.

As discussed above, according to Comparative Example, it is impossible to distinguish *Nisseria gonorrhoeae* in low concentration. On the contrary according to the present invention, in the samples where mixed infections are assumed, it is possible to simultaneously amplify and distinguish multiple genes by means of one reaction vessel containing one kind of reaction solution by means of one kind of labels. This benefit is shown as mentioned above.

TABLE 6

| Samples | DNA | Conc. (copies/ tube) | Detecting first target | | Detecting first and second target | | | |
|---|---|---|---|---|---|---|---|---|
| | | | F1 [23] | Chlam. | C.E.2 | | Emb.1 | |
| | | | | | Fs [23] | N.G. | Fr' [23] | N.G. |
| Sample 1 | STD CT1 | $4.1 \times 10^2$ | 0.92164 | + | −0.0150 | − | 1.1378 | + |
| | STD NG1 | $4.1 \times 10^2$ | | | | | | |
| Sample 2 | STD CT1 | $1.1 \times 10^6$ | 0.7857 | + | −0.0317 | + | 1.1364 | + |
| | STD NG1 | $4.1 \times 10^2$ | | | | | | |
| Sample 3 | STD CT1 | $4.4 \times 10^2$ | 0.8321 | + | −0.1006 | + | 1.8587 | + |
| | STD NG1 | $1.1 \times 10^6$ | | | | | | |

−: Negative
+: Positive

Embodiment 3

<Detection of One Base Sequence Variation within *Mycoplasma* 23 S rRNA Gene According to QProbe Method No. 1>

The *Mycoplasma* 23 S rRNA genes will now be detected according to the QProbe method to distinguish one base sequence variation within the same.
<Material and Steps>
[Primer]

A pair of primers used for the PCR method in Embodiment 3 is as shown in Table 7.

TABLE 7

| Name | Sequence(5'→3') |
|---|---|
| MCR F6 | CTCGGTGAAATCCAGGTACGGGTGAAGAC SEQ No.7 |
| MCR R6 | GCATCGATTGCTCCTACCTATTCTCTACATGATAATGTCC SEQ No. 8 |

(Nucleic Acid Sample)

Nucleic acid samples used for the PCR method in Embodiment 3 are shown below.

It is known that strains resistant to macrolide-based drugs which are antimicrobial agents for *Mycoplasma pneumoniae* have variation in the base sequence of 23S rRNA gene.

Herein, target sequence without the variation in the 23 S rRNA gene and a target sequence wherein a base of "A" in the 2063rd site thereof has varied to another base of "G" are used for nucleic-acid samples, and then PCR is performed thereon, respectively.

Nucleic acid samples used for the PCR method in Embodiment 3 will now be shown below.
(STD MCR1)

*Mycoplasma pneumoniae* is a pathogenic organism of *Mycoplasma* pneumonia. 23 S rRNA is ribosomal RNA derived from *Mycoplasma pneumoniae*. Gene fragments capable of being amplified by means of a pair of primers SEQ. Nos. 7 and 8 of 23S rRNA are artificially synthesized to be incorporated into a pMD20T vector to produce first plasmid DNA. The first plasmid DNA is selected as the first target nucleic acid in Embodiment 3.

The gene fragment is a sequence including 2063rd site and 2064th site of the 23S rRNA, and GenBank Accession No. CP010546 derived from FH strains of *Mycoplasma pneumoniae* is used for the same.

The FH strains are strains sensitive to macrolide, and have 2063rd site thereof has a base of "A". Production of the first plasmid DNA has been performed by requesting custom synthesis to the Takara Bio Inc.

(STD MCR2)

As sequences of the gene fragments, sequences of GenBank Accession No. CP010546 derived from C267 strains of *Mycoplasma pneumoniae* are artificially synthesized to be incorporated into a pMD20T vector to produce second plasmid DNA. The second plasmid DNA is selected as the second target nucleic acid in Embodiment 3. Production of the second plasmid DNA has been performed by requesting custom synthesis to the Takara Bio Inc.

The C267 strains are strains resistant to macrolide, and have sequences wherein a base of "A" in 2063rd site of 23S rRNA gene has varied to another base of "G".

(Preparation of Nucleic Acid Sample)

First length of the STD MCR1 plasmid is 2868 [bp], and second length of the STD MCR2 plasmid is 2868 [bp].

Based on the first and second length and the concentration [µg/□µl] of plasmid solution, the number of copies per 1 [µ 1] has been calculated. After that, by means of TE buffer solution (10 [mM] Tris-HCl, 1.0 [mM] EDTA pH: 8.0), both of the STD MCR1 plasmid and the STD MCR2 plasmid has been diluted to be $1.1 \times 10^2$ [copies/□µl] or $1.1 \times 10^6$ [copies/□µl], respectively.

(Probe)

Amplified STD MCR1 and STD MCR2 are distinguished by means of one kind of QProbes.

Information of the probes used for the PCR method in Embodiment 3 is as shown in Table 8.

TABLE 8

| Name | Sequence(5'→3') |
|---|---|
| MCR QP4 | ACGGAAAGACCCCGTGAAGCTTTAC SEQ No. 9 |

Based on a basic sequence of PCR products of STD MCR1 capable of being amplified by means of a pair of primers in Table 8, a specific region of the No. 9 sequence has been selected referring to Tm values calculated with a QProbe design support tool on the J-Bio21 Center home pages.

"MCR QP4" is one QProbe specifically annealing the STD MCR1 plasmid. As fluorescent dye for "MCR QP4", "BODIPY FL" (registered trademark) has been used to label "C" at 3' end. Production of the QProbes has been performed by requesting custom synthesis to the NIPPON STEEL & SUMIKIN Eco-Tech Corporation.

MCR QP4 is 100% homologous sequence to STD MCR 1. Herein, at a range of temperature lower than a Tm value of MCR QP4, it is expected that MCR QP4 hybridizes not only with STD MCR1 but also with STD MCR2.

(Conditions of PCR and Fluorescence Measurement)

In Embodiment 3, a Tm value of QProbe (MCR QP4) specifically hybridizing with STD MCR1 of the first target nucleic acid is set up to be higher than a Tm value of the primers.

First temperature at which MCR QP4 hybridizes with STD MCR2 of the second target nucleic acid is temperature lower than second temperature at which MCR QP4 hybridizes with STD MCR1 of the first target nucleic acid.

In view of the above, fluorescence intensity is measured to be used for the judgment at:

the second temperature at which MCR QP4 is expected to hybridize with STD MCR1 of the first target nucleic acid; and the first temperature lower than the second temperature.

Table 9 and Table 10 show composition of the PCR reaction solution and the reaction conditions respectively, and FIG. 12 is a graph showing change of temperature within the mixed solution.

The PCR device in the name of "Smart Gene" (registered trademark in Japan) manufactured by the Mizuho Medy Co., Ltd. has been used for the PCR and the fluorescence measurement.

Based of the center wavelength of 525 [nm], excitation wavelength and fluorescent wavelength upon fluorescence measurement have been set up, respectively.

Fluorescence values have been measured at a first step for detecting the first and second target nucleic acid (95 Centigrade and 55 Centigrade) and a second step for detecting the first target nucleic acid (95 Centigrade and 66 Centigrade) during the amplification reaction.

TABLE 9

| Solution composition | Final concentration |
|---|---|
| Solution composition | |
| MilliQ water(™) | — |
| PCR buffer | ×1 |
| dNTP Mix | 150 μM |
| MCR F6 | 0.180 μM |
| MCR R6 | 0.540 μM |
| MCR QP4 | 0.090 μM |
| KOD exo (−) DNA Polymerase | 0.0125 U/μL |
| target NA | |

Prepared to be μL

TABLE 10

| Reaction stage | Temperature (° C.) | | Time (Sec) |
|---|---|---|---|
| Early denaturation Amp reaction (1-23 cycle) | 95 | T0 | 120 |
| Detecting first and second target | 95 | T0 | 10 (Measure FL) |
| | 55 | T3 | 10 (Measure FL) |
| Detecting first target | 95 | T0 | 10 (Measure FL) |
| | 66 | T2 => T1 | 10 (Measure FL) |

(How to Handle Data)

As analysis by means of the QProbes, correction calculation has been performed on obtained raw data by the same procedures as Embodiment 1.

For every cycle during the amplification reaction, a fluorescence intensity value f1[n] in the first target detection step in n-th cycle is calculated by means of the Formula 1.

As first values for this calculation, a fluorescence intensity value fhyb.1[n] at 66 Centigrade in the first target detection step and an intensity value fden.1[n] at 95 Centigrade in the first target detection step are used.

Similar to the above, for every cycle during the amplification reaction, a fluorescence intensity value f2[n] in the first and second target detection step in n-th cycle is calculated by means of the Formula 1'.

As second values for this calculation, a fluorescence intensity value fhyb.2[n] at 55 Centigrade in the first and second target detection step and an intensity value fden.2[n] at 95 Centigrade in the first and second target detection step are used.

Next, for every cycle of the amplification reaction, a number of "10" is substituted for X in the Formula 3, and a fluorescence intensity value f1[10] in tenth cycle obtained according to the Formula 1 is assumed to be a number of "1". And then, a relative value F1 [n] in n-th cycle is calculated.

In addition, a number of "10" is substituted for X in the Formula 3', and a fluorescence intensity value f2[10] in tenth cycle obtained according to the Formula 1' is assumed to be a number of "1". And then, a relative value F2 [n] in n-th cycle is calculated.

The value of F2 [n] is a value that reflects not only first change of first fluorescent signals caused by amplification of the first target nucleic acid but also second change of second fluorescent signals caused by amplification of the second target nucleic acid.

Accordingly in Embodiment 3, the value of F2 [23], which is the value of F2 [n] in the final cycle of the amplification reaction, is used for judgment of existence/non-existence of the first target nucleic acid and the second target nucleic acid, that is, judgment with respect to *Mycoplasma* infection.

In addition, a number of "1.05" is substituted for the constant "a" in the Formula 2', and the value of Fr' [n] is calculated.

Values of Fr[23] and Fr' [23], which are values of Fr' [n] and Fr' [23] in the final cycle of the amplification reaction, are used for judgment of the second target nucleic acid.

When the second target nucleic acid is positive, it is revealed that *Mycoplasma* is positive and further that the target nucleic acid has drug resistance variation therein.

A Tm value for the sequence of MCR QP4 is set up to be 71 Centigrade. It is supposed that the probe MCR QP4 during PCR anneals only to STD MCR1 in the first detection step (95 Centigrade and 66 Centigrade), and anneals to both of STD MCR1 and STD MCR2 in the second detection step (95 Centigrade and 55 Centigrade).

An amplification curve will now be generated by plotting the values of F1[n] and F2 [n] during the amplification reaction.

Regarding an amplification curve of the negative reference (sample wherein TE buffer solution is added thereto instead of DNA), quenching light has not been observed until 23-rd cycle when the PCR ends. FIG. 13 shows the amplification curve related thereto.

Regarding STD MCR1 of $1.1 \times 10^2$ [copies/tube], quenching light with respect to both of the values of F1[n] and F2 [n] caused by annealing of MCR QP4 has been observed from near 20th cycle on the amplification curve. FIG. 14 shows the amplification curve related thereto.

Regarding STD MCR1 of $1.1 \times 10^6$ [copies/tube], quenching light with respect to both of the values of F1[n] and F2 [n] caused by annealing of MCR QP4 has been observed from near 12th cycle on the amplification curve. FIG. 15 shows the amplification curve related thereto.

Regarding STD MCR2 of $1.1 \times 10^2$ [copies/tube], quenching light with respect to the value of F2 [n] caused by annealing of MCR QP4 has been observed from near 22nd cycle on the amplification curve. On the contrary, quenching light exceeding the threshold (mentioned below) of the value of F1 [n] has not been observed until 23-rd cycle when the PCR ends. FIG. 16 shows the amplification curve related thereto.

Regarding STD MCR2 of $1.1 \times 10^6$ [copies/tube], quenching light with respect to the value of F2 [n] caused by annealing of MCR QP4 has been observed from near 12th cycle on the amplification curve.

In addition, quenching light with respect to the value of F1[n] caused by annealing of MCR QP4 has been observed from near 15th cycle on the amplification curve.

When STD MCR2 is contained in high concentration, quenching light caused by conjunction of MCR QP4 and STD MCR2 may interferes the value of F1 [n]. This may be supposed as a reason why the above phenomenon occurs. FIG. 17 shows the amplification curve related thereto.
(Judgment of *Mycoplasma*)

The value of F2 [23], which is the value of F2 [n] in the final cycle during the amplification reaction is used for the judgment with respect to *Mycoplasma* infection.

Threshold 4 of 0.9985 is used as a threshold for the judgment. Herein, Threshold 4=the average value of Fs [23] of the negative reference −3*the standard deviation of Fs [23] of the negative reference.

The value of F2 [23] is compared with Threshold 4. When F2[23] is less than Threshold 4, it is jugged to be *Mycoplasma* positive.

Since 1.0070 of F2 [23] with respect to the negative reference is not greater than Threshold 4, it is judged to be *Mycoplasma* negative.

Since all the values of F2 [23] with respect to samples wherein STD MCR1 or STD MCR2 are added thereto are less than Threshold 4, the samples are judged to be *Mycoplasma* positive.
(Judgment of Second Target Nucleic Acid)

The judgment according to the present invention will now be performed as follows.

In Embodiment 3, calculated values of $$Fr'[23]=(1.02-F2[23])/(1.02-F1[23])]$$

is used for judgment with respect to STD MCR2 of the second target nucleic acid.

Threshold 5 of 2.8966 (N=10) is used as a threshold for the judgment. Herein, Threshold 5=the average value of calculated values Fr' [23]−3*the standard deviation of the calculated values Fr' [23], both of which being related to STD MCR1 of $1.1 \times 10^6$ [copies/tube].

When the value of Fr'[23] is greater than Threshold 5, it is judged to be second target positive.

Since all of the value of 0.9398, which is the calculated value Fr'[23] with respect to the negative reference, the value of 1.6209 (calculated value Fr'[23] with respect to STD MCR1 of $1.1 \times 10^6$ [copies/tube]), and the value of 1.6153 (calculated value Fr'[23] with respect to STD MCR1 of $1.1 \times 10^6$ [copies/tube]) are less than Threshold 5, they are judged to be the second target negative.

Since the value of 3.8210 (calculated value Fr'[23] with respect to STD MCR2 of $1.1 \times 10^2$ [copies/tube]), and the value of 6.1236 (calculated value Fr'[23] with respect to STD MCR2 of $1.1 \times 10^6$ [copies/tube]) are greater than Threshold 5, they are judged to be the second target positive.

Comparative Example 3

By means of the same procedures as Comparative Example 1, judgment with respect to the second target nucleic acid will now be performed as follows.

Threshold 6 of −0.1775 (N=10) is used as a threshold for the judgment. Herein, Threshold 6=the average value of calculated values Fs [23]−3*the standard deviation of the calculated values Fs [23], both of which being related to STD MCR1 of $1.1 \times 10^6$ [copies/tube].

When the value of Fs[23] is less than Threshold 6, it is judged to be second target positive.

Since all of the value of 0.0008, which is the calculated value Fs[23] with respect to the negative reference, the value of −0.0448 (calculated value Fs[23] with respect to STD MCR1 of $1.1 \times 10^6$ [copies/tube]), the value of −0.0990 (calculated value Fs[23] with respect to STD MCR2 of $1.1 \times 10^2$ [copies/tube]), the value of −0.0568 (calculated value Fs[23] with respect to STD MCR2 of $1.1 \times 10^2$ [copies/tube]), and the value of −0.1732 (calculated value Fs[23] with respect to STD MCR2 of $1.1 \times 10^6$ [copies/tube]) are greater than Threshold 6, they are judged to be the second target negative.

Table 11 shows: the relative fluorescence value F2[23] in 23rd cycle; the results of *Mycoplasma* judgment; and the judgment results with respect to *Mycoplasma* variation in Comparative Example 2 and Embodiment 2.

As mentioned above, according to analysis in the Comparative Example, even in a case wherein *Mycoplasma* is positive, it is revealed that existence of the variation cannot be distinguished.

This is because it is impossible to discriminate between a first change amount of Fs [23] caused by concentration thereof and a second change amount of Fs [23] caused by STD MCR2.

On the contrary, according to the present invention even in a case wherein first detection temperature of the first target nucleic acid and second detection temperature of the second target nucleic acid are close to each other so that fluorescent signals at the first and second temperature must interfere mutually, it is revealed that it is possible to simultaneously amplify and distinguish multiple genes by means of one reaction vessel containing one kind of reaction solution by means of one kind of labels without being influenced by the concentration of the first target nucleic acid.

TABLE 11

| DNA | Conc. (copies/tube) | First and second target F2[23] | First and second target Mycop. | Second target C.E.3 Fs[23] | Second target C.E.3 variation | Second target Emb.3 Fr'[23] | Second target Emb.3 variation |
|---|---|---|---|---|---|---|---|
| N Ref | 0 | 1.0070 | Negative | 0.0008 | – | 0.9398 | – |
| STD MCR1 | $1.1 \times 10^2$ | 0.9030 | Negative | −0.0448 | – | 1.6209 | – |
| STD MCR1 | $1.1 \times 10^6$ | 0.7601 | Negative | −0.0990 | – | 1.6153 | – |
| STD MCR2 | $1.1 \times 10^2$ | 0.9130 | Negative | −0.0568 | – | 3.8210 | + |
| STD MCR2 | $1.1 \times 10^6$ | 0.8129 | Negative | −0.1732 | – | 6.1236 | + |

–: Not varied
+: Varied

Embodiment 4

<Detection of One Base Sequence Variation within *Mycoplasma* 23 S rRNA Gene According to QProbe Method No. 2>

When the present invention is applied to Embodiment 3, it is suggested that the second target nucleic acid can be distinguished without being influenced by the concentration of the first target nucleic acid.

In Embodiment 4, while using the same conditions as Embodiment 3, samples of three sets of concentration of the first target nucleic acid and the second target nucleic acid are measured, respectively. A calculated value Fs[23] for judgment of the second target nucleic acid according to Comparative Example and a calculated value Fr' [23] for judgment of the second target nucleic acid according to the present invention are calculated. And then, behavior of the calculated values is compared there-with.
(Nucleic Acid Sample)

Nucleic acid samples used for the PCR method in Embodiment 4 are shown below.
(Preparation of Nucleic Acid Sample)

By means of TE buffer solution (10 [mM] Tris-HCl, 1.0 [mM] EDTA pH: 8.0), both of the STD MCR1 plasmid and the STD MCR2 plasmid has been diluted to be 10 [copies/□µl], 40 [copies/□µl] or $1 \times 10^6$ [copies/□µl] to produce ten samples to be measured, respectively.
(Judgment of *Mycoplasma*)

While using the same method as Embodiment 3, the values of F2 [23] in the final cycle during the amplification reaction are compared with Threshold 4 to judge existence/non-existence of *Mycoplasma*.

Herein, data at this time is not shown. However, as the result, the values of F2 [23] in all samples are less than Threshold 4, and all of them are judged to be *Mycoplasma* positive.
(Judgment of Second Target Nucleic Acid)

Next, while using the same procedures as Embodiment 3, judgment according to the present invention will now be performed. FIG. 18 shows the results with respect to the values of Fr'[23] related thereto.

The values of Fr'[23] keep a fixed value that is not influenced by the concentration of the first target nucleic acid. Herein, as the concentration of the second target nucleic acid is higher, the fixed value becomes higher.

Upon measuring the samples containing the first target nucleic acid, the values of Fr' [n] keeps the fixed value because both of values of F1 [n] and F2 [n] increase/decrease in a fixed ratio to the concentration of the first target nucleic acid. On the other hand, upon measuring the samples containing the second target nucleic acid, the values of Fr' [n] change depending upon the concentration of the second target nucleic acid because only the values of F2[n] change depending upon the concentration of the second target nucleic acid. The above results reveal this relationship.

Comparative Example 4

While using the same procedures as Embodiment 3, judgment according to Comparative Example 4 will now be performed.

FIG. 19 shows the results with respect to the values of Fr[23] related thereto.

As concentration increases, both of calculated values of STD MCR1 and STD MCR2 become smaller. Only the value of Fs [23] of the second target nucleic acid having concentration of $1 \times 10^6$ [copies/□µl] STD MCR2 can be distinguished from the value Fs [23] of the first target nucleic acid.

The above results reveal that the present invention enables to judge the second target nucleic acid without being influenced by existence/non-existence of the first target nucleic acid.

Embodiment 5

<Melting Curve Analysis Method According to QProbe Method>

The melting curve analysis is one of methods for simultaneously detecting multiple genes by means of one reaction vessel containing one kind of reaction solution by means of one kind of labels.

Regarding PCR products, labeling probes, and so on, when dissociation temperature thereof cannot be enough separated there-from, melting temperature (dissolution peaks) of multiple targets become closer. This relationship must make distinction from each other difficult.

It is thought that fluorescent signals change in almost the same way between in a first case during the PCR and a second case wherein the melting curve analysis method is performed. For this reason, it may be expected to apply the present invention also to the melting curve analysis successfully.
(How to Handle Data)

After the PCR has been completed, the measurement shown in Embodiment 3 is performed for melting curve analysis.

More concretely in Embodiment 5,
firstly, the PCR has been completed,
secondly, the melting curve analysis in Embodiment 3 is performed to obtain data,
thirdly, while using the obtained data, it will be inspected whether or not the first target nucleic acid and the second target nucleic acid can be distinguished from each other by the melting curve analysis to which the method according to the present inventing has been applied.

The melting curve analysis is performed within a range from 55 Centigrade to 80 Centigrade. Raw data of fluorescence intensity is taken out. And then by means of the Formula 4, a fluorescence intensity value f1m in the first target detection step with respect to the melting curve is calculated.

As values for this calculation with respect to the melting curve analysis, a first fluorescence intensity value fhyb.1m at 66 Centigrade, which is the first probe for first target hybridization temperature, and a second fluorescence intensity value fden.1m at 80 Centigrade, which is the first probe for first target dissociation temperature, are used.

Similar to the above by means of the Formula 4', a second fluorescence intensity value f2m in the second target detection step with respect to the melting curve is calculated.

As values for this calculation with respect to the melting curve analysis, a third fluorescence intensity value fhyb.2m at 66 Centigrade, which is the first probe for first target and the second prove for second target hybridization temperature, and a fourth fluorescence intensity value fden.2m at 80 Centigrade, which is the first probe for first target and the second probe for second target dissociation temperature, are used.

FIG. 20 is a graph showing relative values of fluorescence intensity under temperature change assuming fluorescence intensity at 80 Centigrade to be a number of "1" (hereinafter, called as "fluorescence relative value").

In the sample wherein STD MCR1 is added thereto, the fluorescence relative values suddenly become high near from 68 Centigrade to 73 Centigrade. This phenomenon reveals that MCR QP4 anneals with STD MCR1 within this temperature range so as to change the fluorescence intensity.

In addition, in the sample wherein STD MCR2 is added thereto, the fluorescence relative values suddenly become high near from 62 Centigrade to 69 Centigrade. This phenomenon reveals that MCR QP4 anneals with STD MCR2 within this temperature range so as to change the fluorescence intensity.

(Judgment of Existence/Non-Existence of *Mycoplasma*)

When a value of f2m, which is a fluorescence relative value at 55 Centigrade, is less than the number of "1", which is the fluorescence relative value at 80 Centigrade, it is judged to be *Mycoplasma* positive.

With respect to the negative reference, since f2m=1.0524, it is judged to be *Mycoplasma* negative.

Herein, f2m of $1.1 \times 10^2$ [copies/tube] STD MCR 1=0.8853, f2m of $1.1 \times 10^6$ [copies/tube] STD MCR1=0.8417, f2m of $1.1 \times 10^2$ [copies/tube] STD MCR2=0.9251, and f2m of $1.1 \times 10^6$ [copies/tube] STD MCR2=0.8437. Thus, all of these are judged to be *Mycoplasma* positive.

(Judgment of Second Target Nucleic Acid)

A value of "1.0524" is substituted to a fixed number "a" in the Formula 5 to calculate a value of Frm.

Herein, Frm of $1.1 \times 10^2$ [copies/tube] STD MCR1=2.5567, and Frm of $1.1 \times 10^6$ [copies/tube] STD MCR1=1.9943.

Similar to Embodiments 1 through 4, in this Embodiment, it is revealed that values of Frm are almost constant without being affected by concentration of the first target nucleic acid.

In view of the above, Threshold 7, which is a threshold for distinguishing the second target nucleic acid, is set to be 2.5567. When Frm is greater than Threshold 7, it is judged to be second target nucleic acid positive.

Herein, Frm of $1.1 \times 10^2$ [copies/tube] STD MCR2=5.5713, and Frm of $1.1 \times 10^6$ [copies/tube] STD MCR2=6.7274.

Since these values are greater than Threshold 7, the samples are judged to be STD MCR2 positive.

Regarding the respective samples, Table 12 shows: values of f2m; the results of *Mycoplasma* judgment; values of frm; and the judgment results with respect to *Mycoplasma* variation.

As discussed above in detail, it is shown that the present invention enables to distinguish a plurality of targets based on data with respect to fluorescence intensity in the melting curve analysis without performing complicated calculation such as a differential equation and/or an approximate expression for calculating a peak of melting temperature.

TABLE 12

| DNA | Conc. (copies/tube) | First and second target | | Second target | |
|---|---|---|---|---|---|
| | | f2m | Mycop. | frm | variation |
| N Ref | 0 | 1.0524 | Negative | 0.0000 | Negative |
| STD MCR1 | $1.1 \times 10^{\wedge}2$ | 0.8853 | Negative | 2.5567 | Negative |
| STD MCR1 | $1.1 \times 10^{\wedge}6$ | 0.8417 | Negative | 1.9943 | Negative |
| STD MCR2 | $1.1 \times 10^{\wedge}2$ | 0.9251 | Negative | 5.5713 | Negative |
| STD MCR2 | $1.1 \times 10^{\wedge}6$ | 0.8437 | Negative | 6.7274 | Negative |

BRIEF DESCRIPTION OF THE DRAWINGS

FIG. 23 (b) is an explanatory view of an annealing step in Embodiment 1 of the present invention;

FIG. 23 (c) is an explanatory view of an elongation step in Embodiment 1 of the present invention;

FIG. 23 (d) is an explanatory view of an elongation-completing in Embodiment 1 of the present invention;

FIG. 24 (b) is an explanatory view of an annealing step in Embodiment 1 of the present invention.

BRIEF DESCRIPTION OF SYMBOLS

Figure 1:
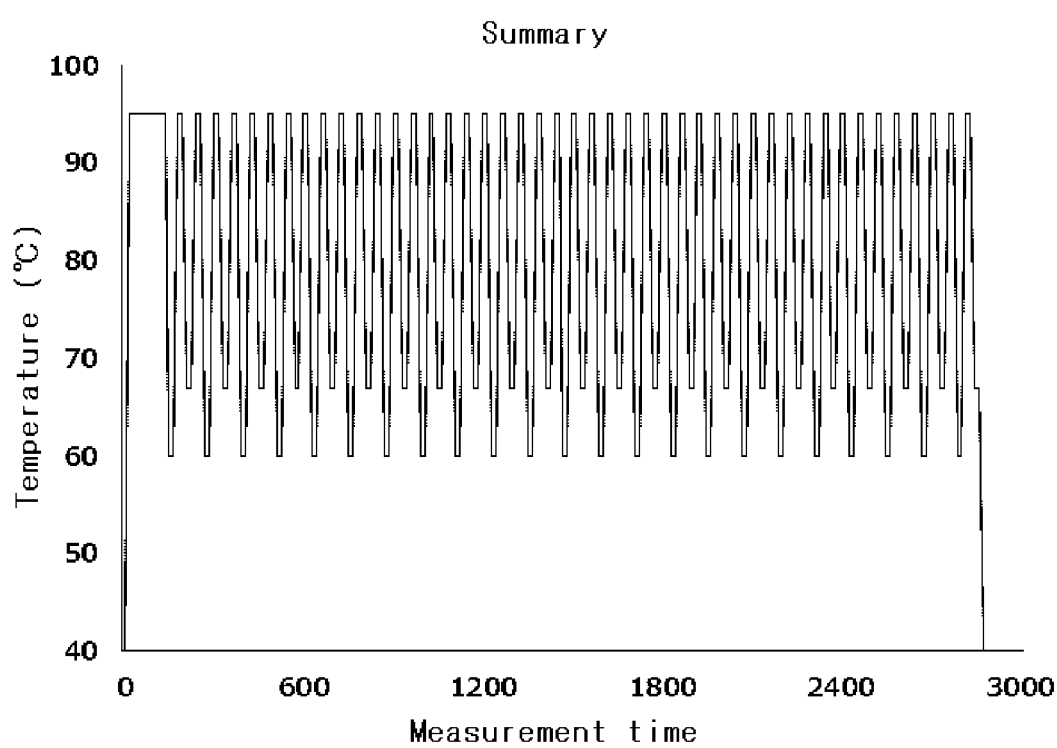
FIG. 1 is a graph showing how temperature within mixed solution in Embodiment 1 of the present invention changes.
Figure 2:
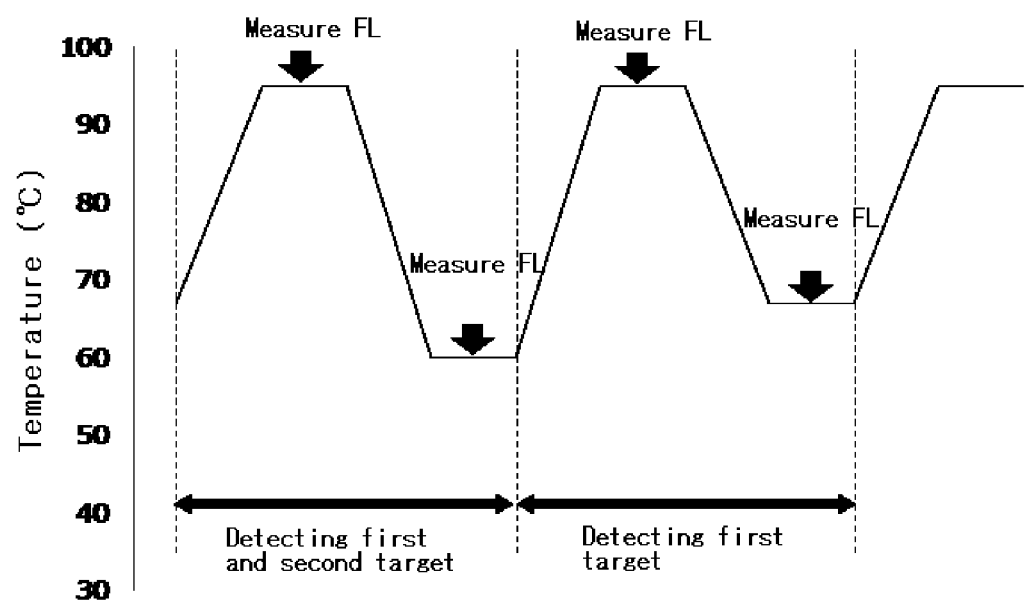
FIG. 2 a diagram showing timing of fluorescence measurement in Embodiment 1 of the present invention.
Figure 3:
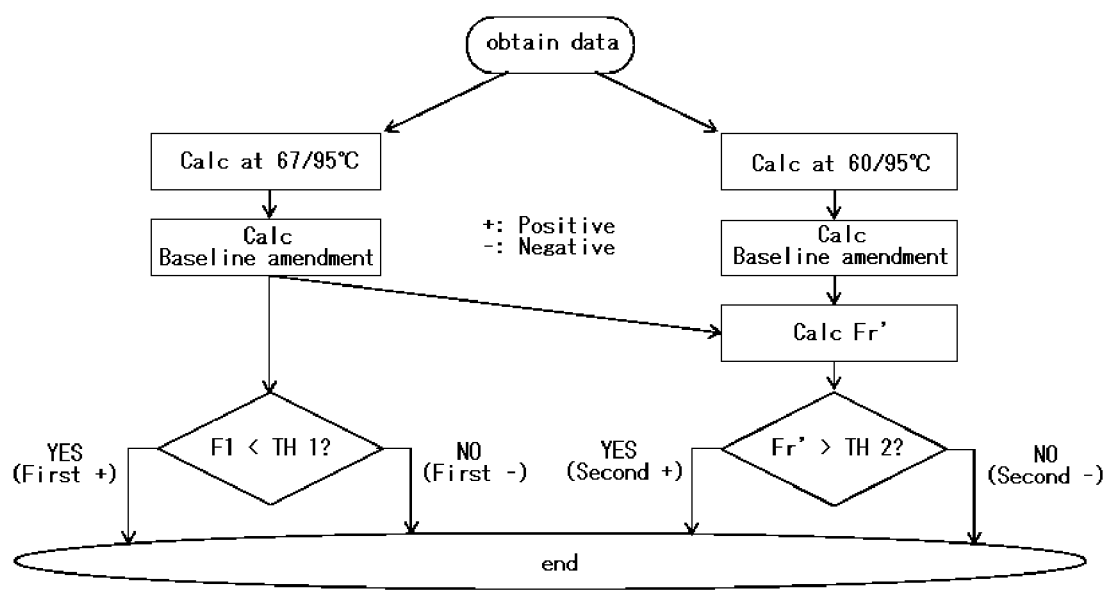
FIG. 3 is a flowchart of a judgment method in Embodiment 1 of the present invention.
Figure 4:
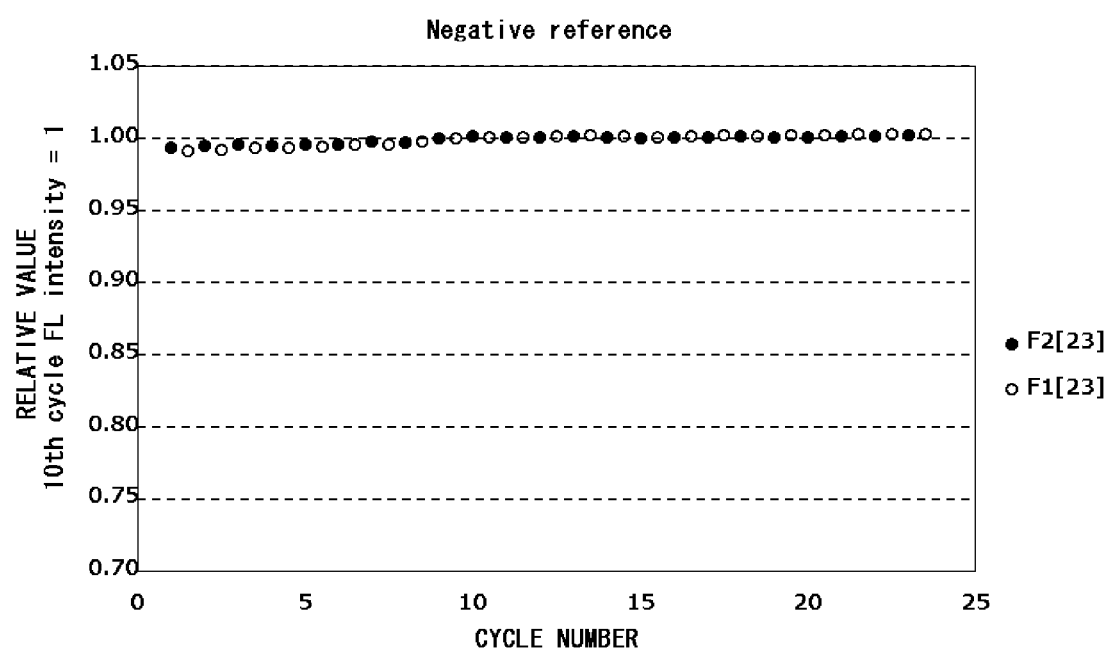
FIG. 4 is a graph showing how fluorescence intensity of a negative reference in Embodiment 1 of the present invention changes.
Figure 5:
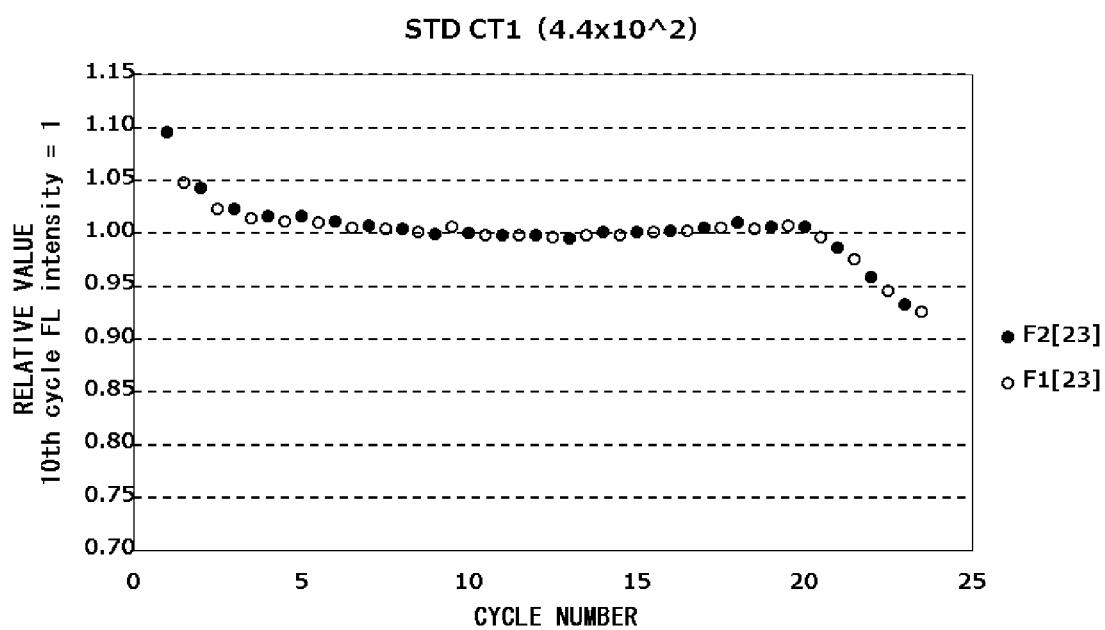
FIG. 5 is a graph showing how fluorescence intensity of first target nucleic acid (low concentration) in Embodiment 1 of the present invention changes.
Figure 6:
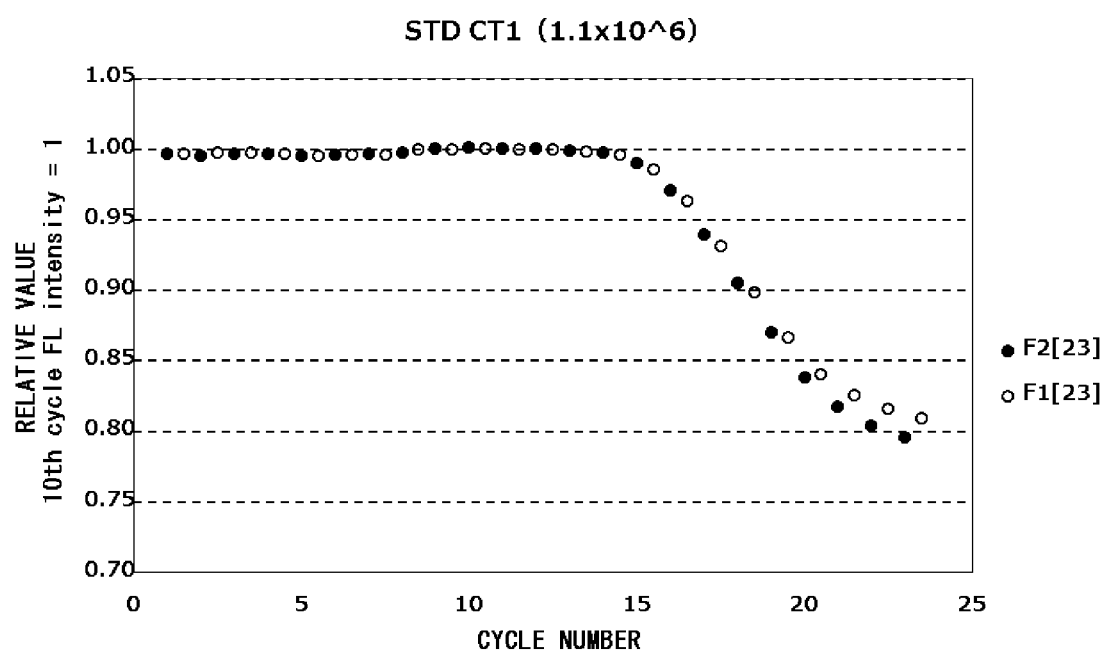
FIG. 6 is a graph showing how fluorescence intensity of first target nucleic acid (high concentration) in Embodiment 1 of the present invention changes.
Figure 7:
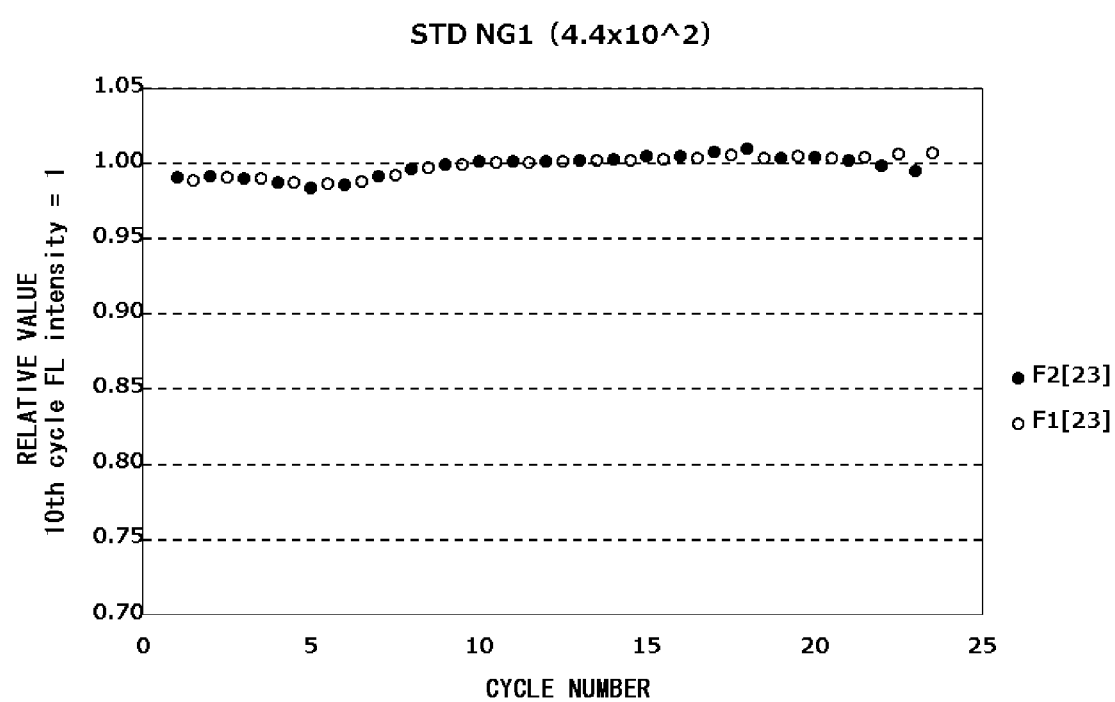
FIG. 7 is a graph showing how fluorescence intensity of second target nucleic acid (low concentration) in Embodiment 1 of the present invention changes.
Figure 8:
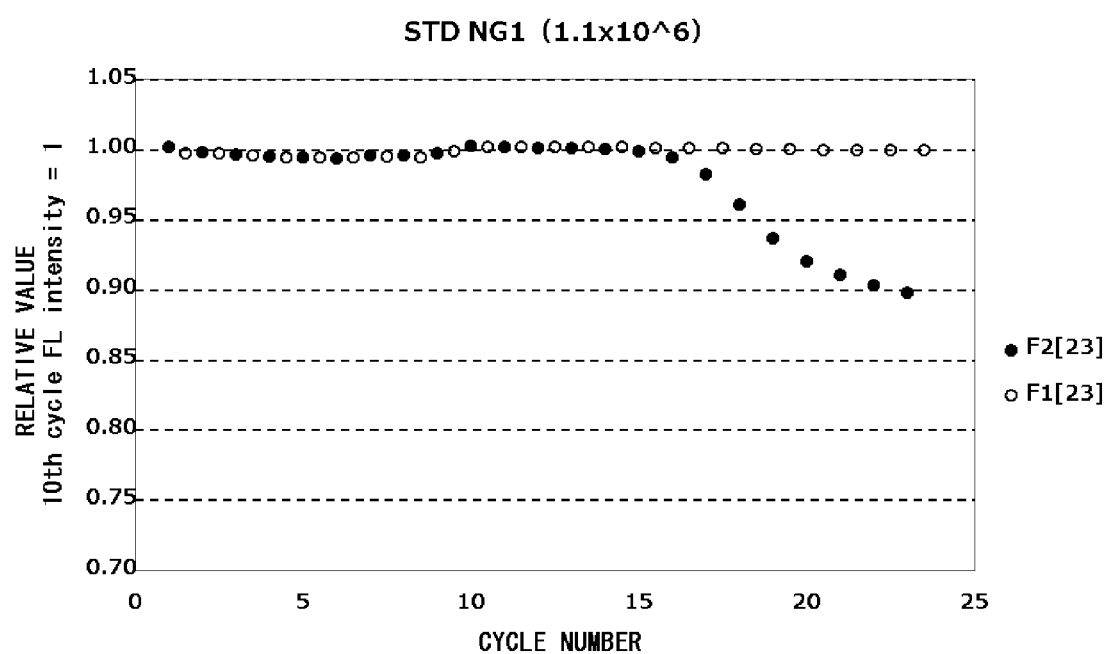
FIG. 8 is a graph showing how fluorescence intensity of second target nucleic acid (high concentration) in Embodiment 1 of the present invention changes.
Figure 9:
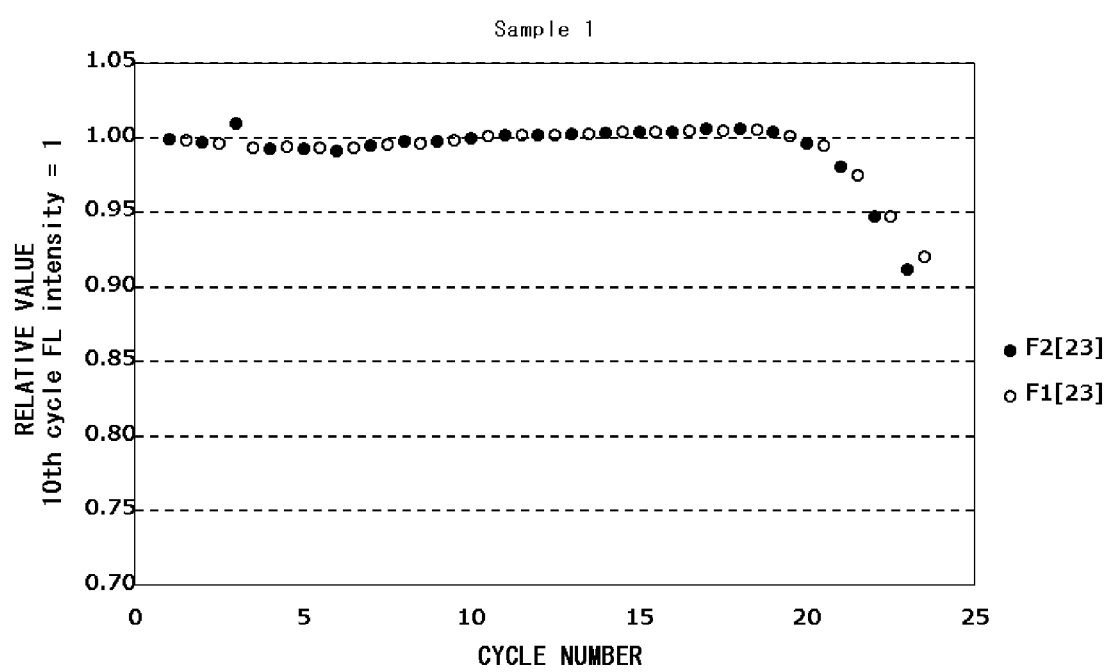
FIG. 9 is a graph showing how fluorescence intensity of (low concentration) first labeling substance and (low concentration) second target nucleic acid in Embodiment 2 of the present invention changes.
Figure 10:
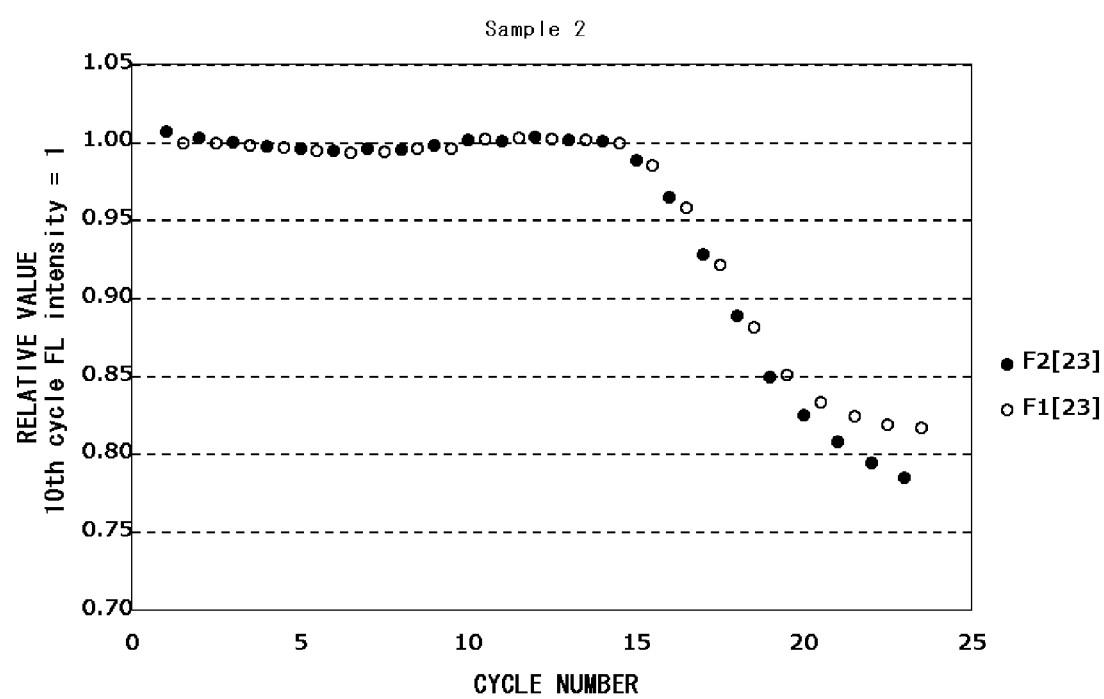
FIG. 10 is a graph showing how fluorescence intensity of (high concentration) first labeling substance and (low concentration) second target nucleic acid in Embodiment 2 of the present invention changes.
Figure 11:
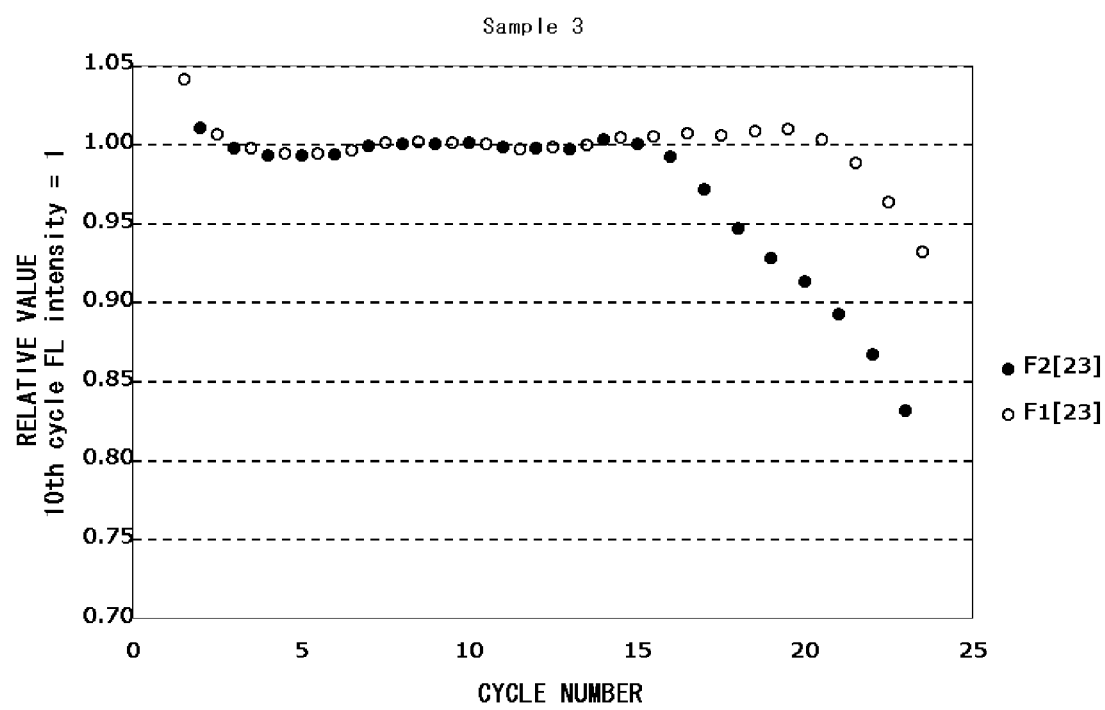
FIG. 11 is a graph showing how fluorescence intensity of (low concentration) first labeling substance and (high concentration) second target nucleic acid in Embodiment 2 of the present invention changes.
Figure 12:
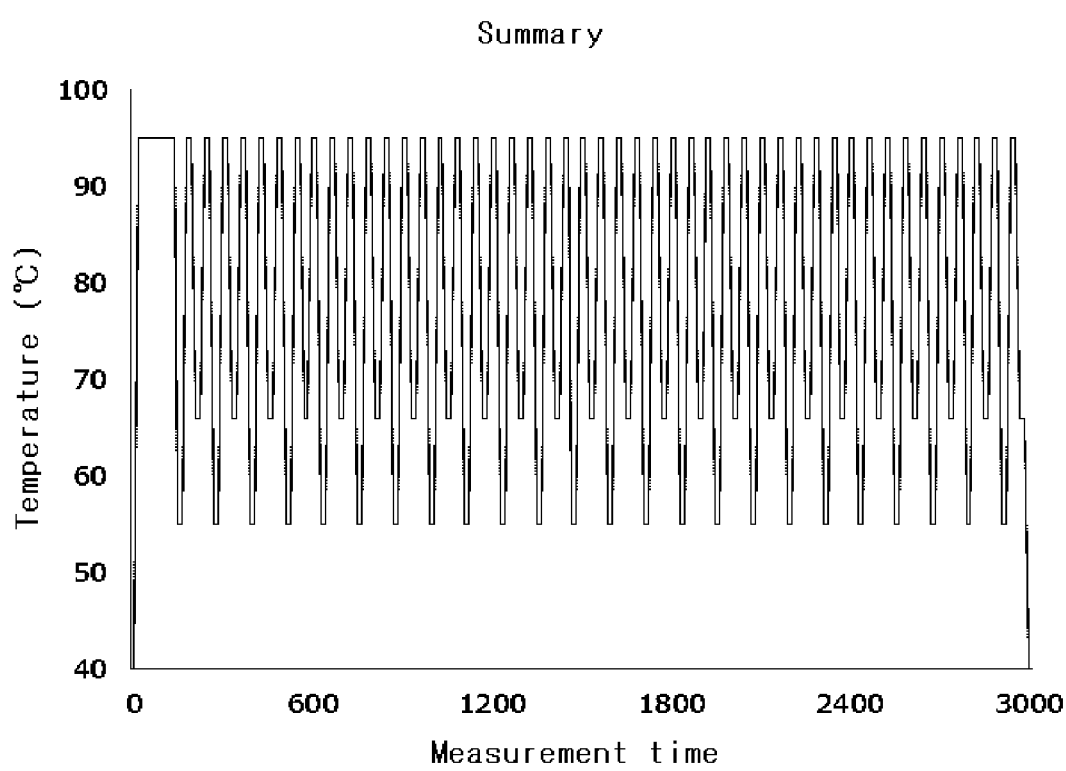
FIG. 12 is a graph showing how temperature within mixed solution in Embodiment 3 of the present invention changes.
Figure 13:
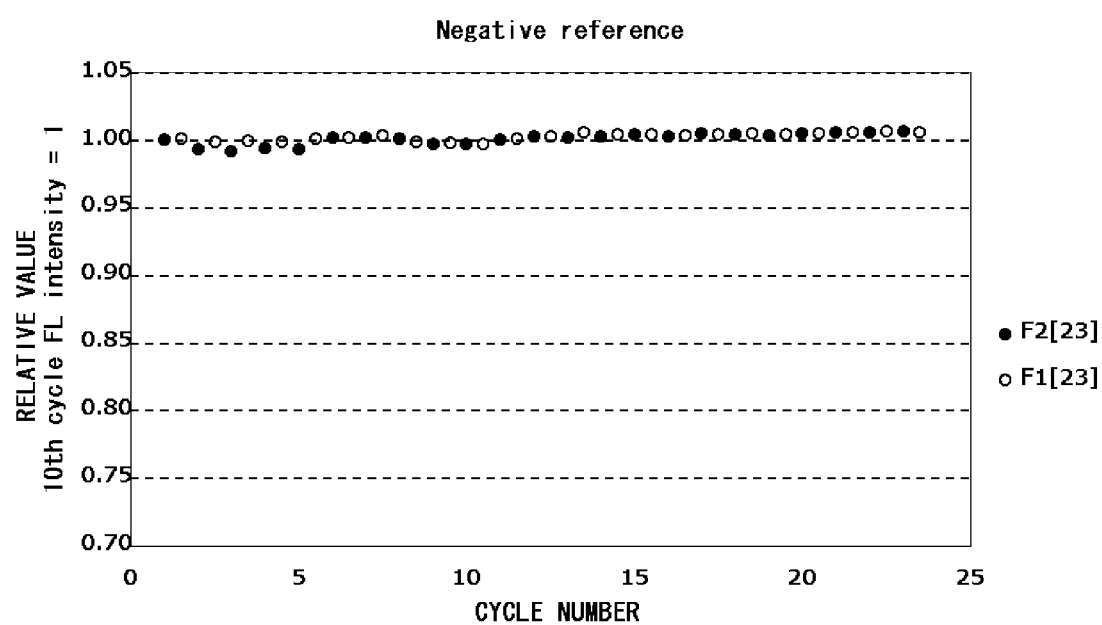
FIG. 13 is a graph showing how fluorescence intensity of a negative reference in Embodiment 3 of the present invention changes.
Figure 14:
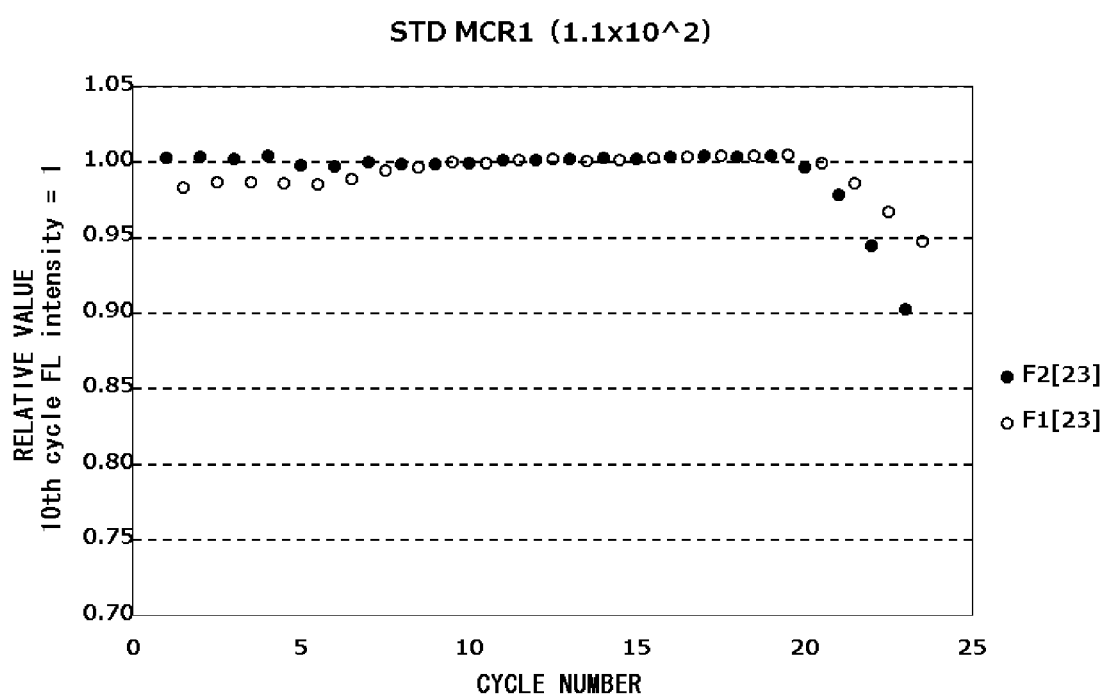
FIG. 14 is a graph showing how fluorescence intensity of first target nucleic acid (low concentration) in Embodiment 3 of the present invention changes.
Figure 15:
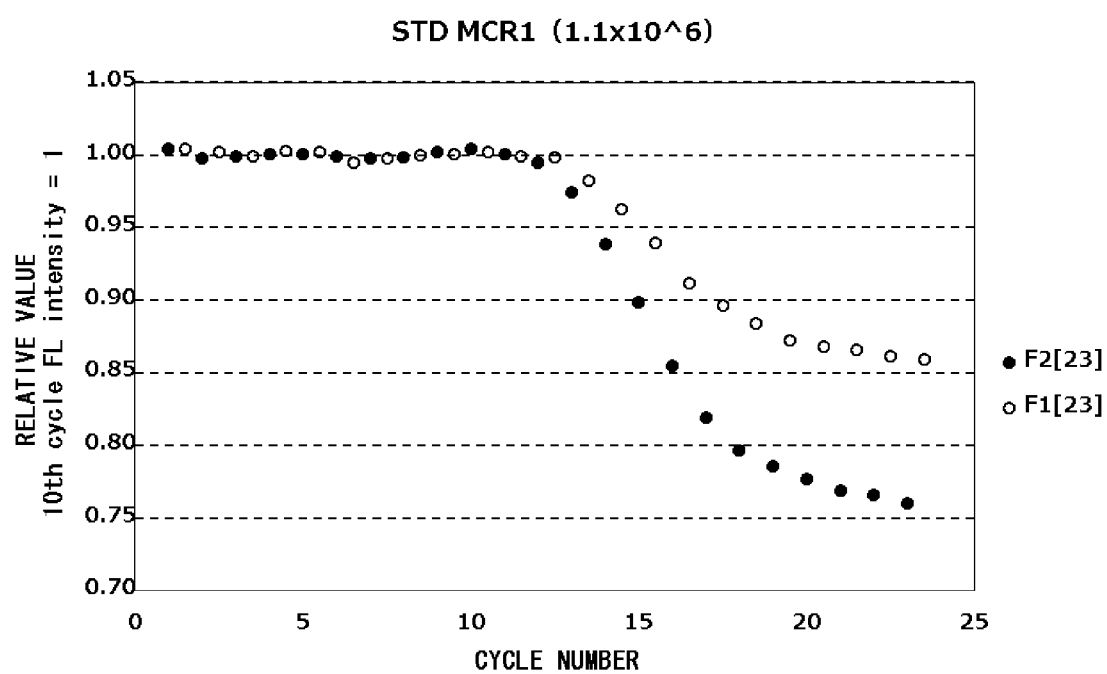
FIG. 15 is a graph showing how fluorescence intensity of first target nucleic acid (high concentration) in Embodiment 3 of the present invention changes.
Figure 16:
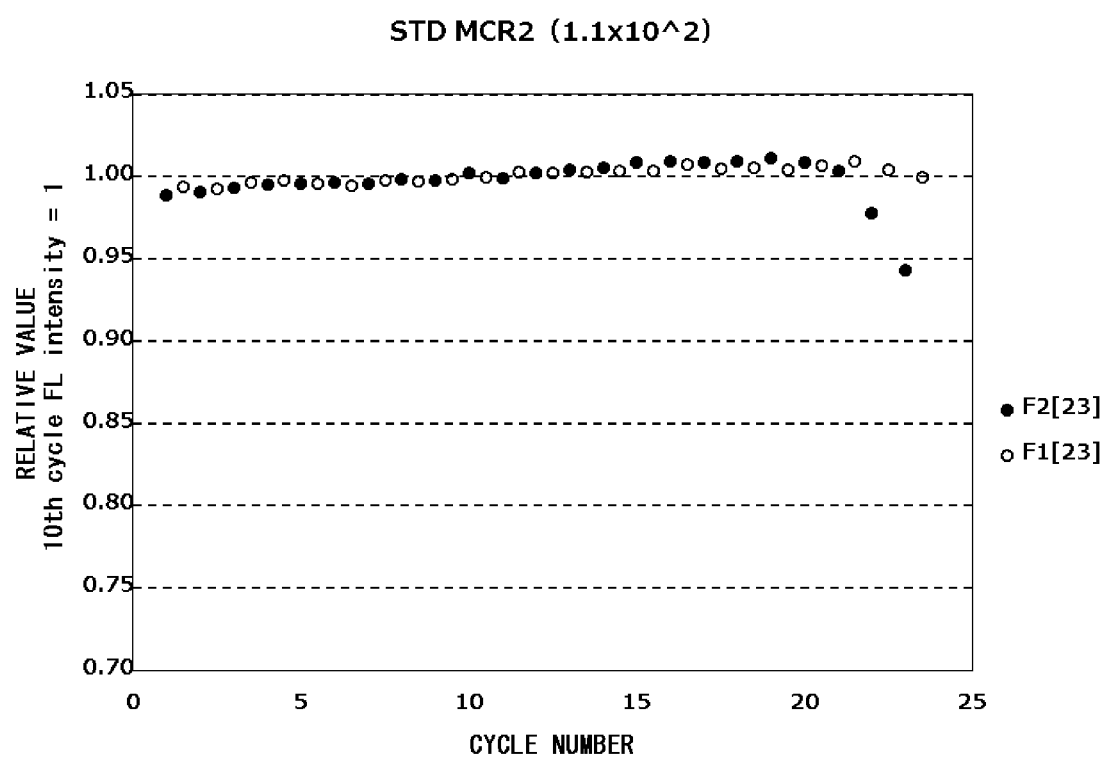
FIG. 16 is a graph showing how fluorescence intensity of second target nucleic acid (low concentration) in Embodiment 3 of the present invention changes.
Figure 17:
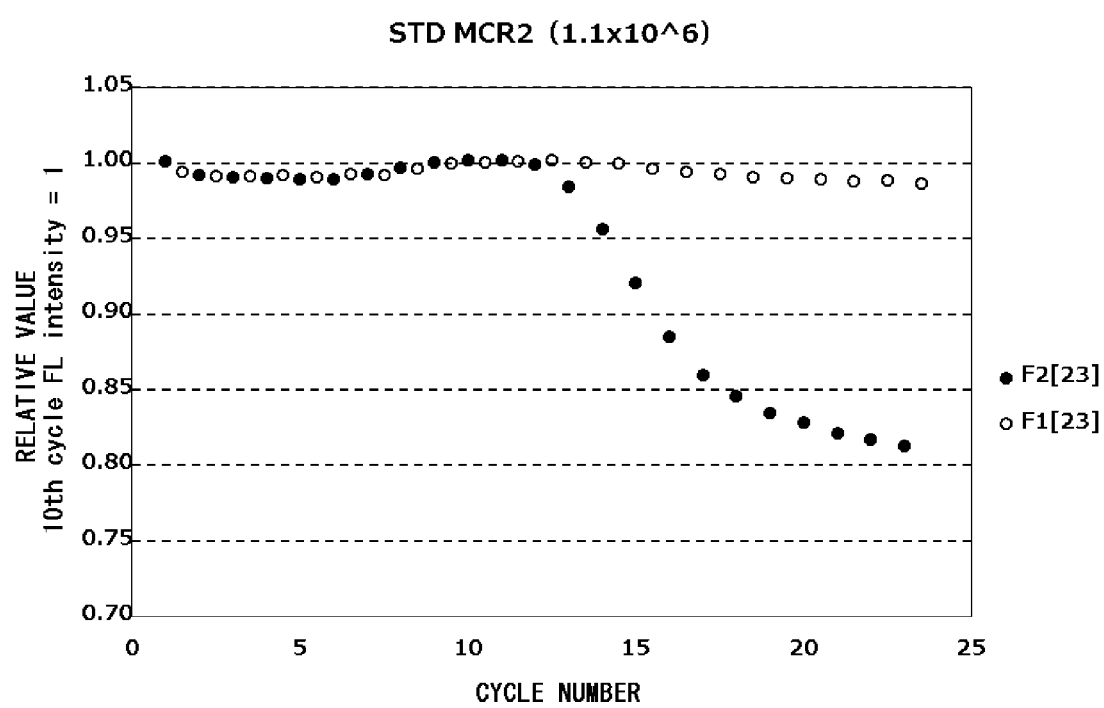
FIG. 17 is a graph showing how fluorescence intensity of second target nucleic acid (high concentration) in Embodiment 3 of the present invention changes.
Figure 18:
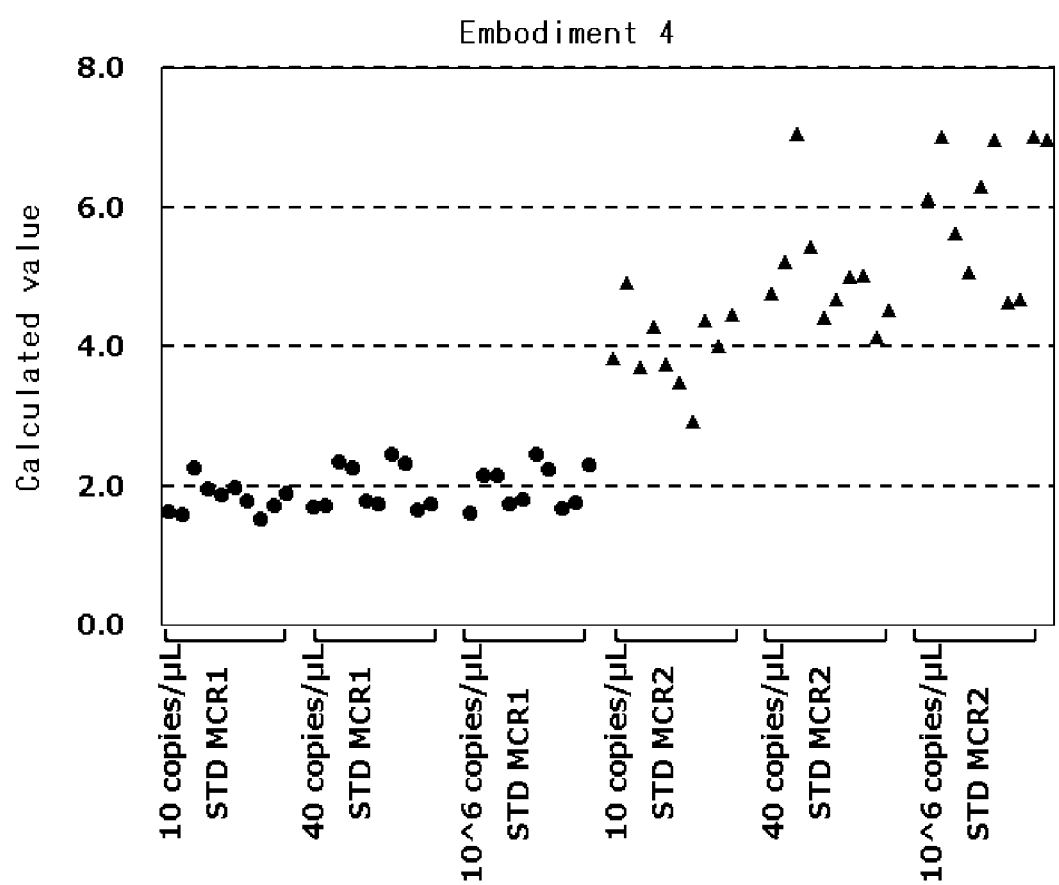
FIG. 18 is a graph showing how Fr calculated values of first labeling substance and second target nucleic acid in Embodiment 4 of the present invention change.
Figure 19:
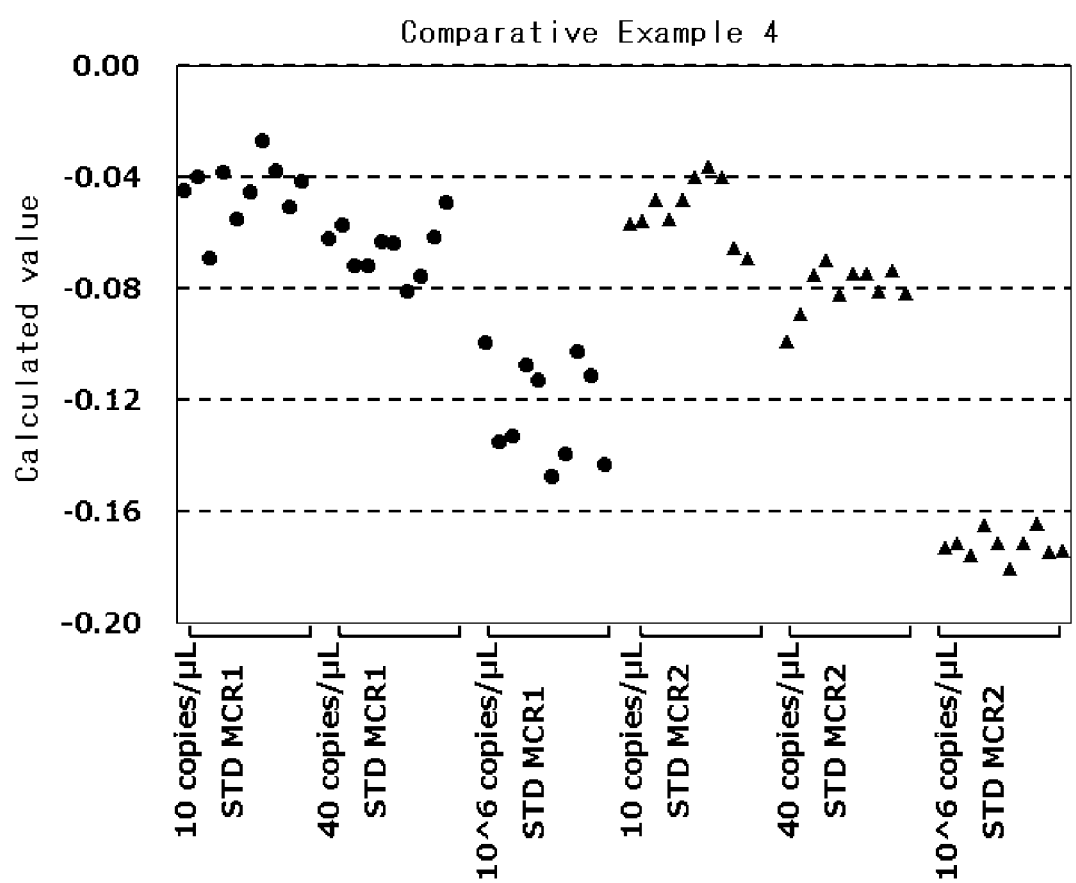
FIG. 19 is a graph showing how Fr calculated values of first labeling substance and second target nucleic acid in Comparative Example 4 of the present invention change.
Figure 20:
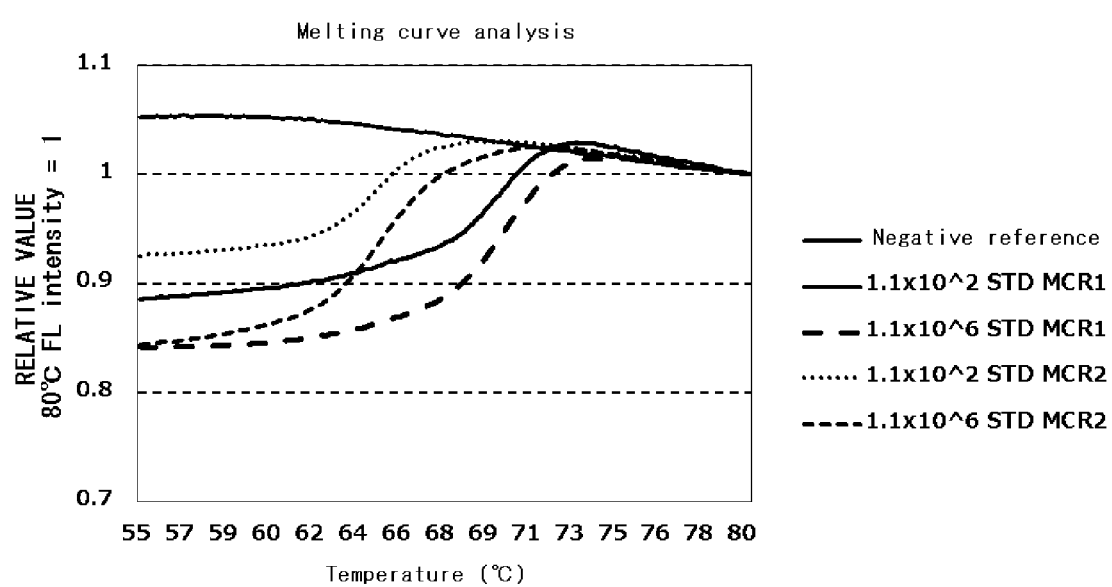
FIG. 20 is a graph showing how fluorescence intensity of a melting curve in Embodiment 5 of the present invention changes.
Figure 21:
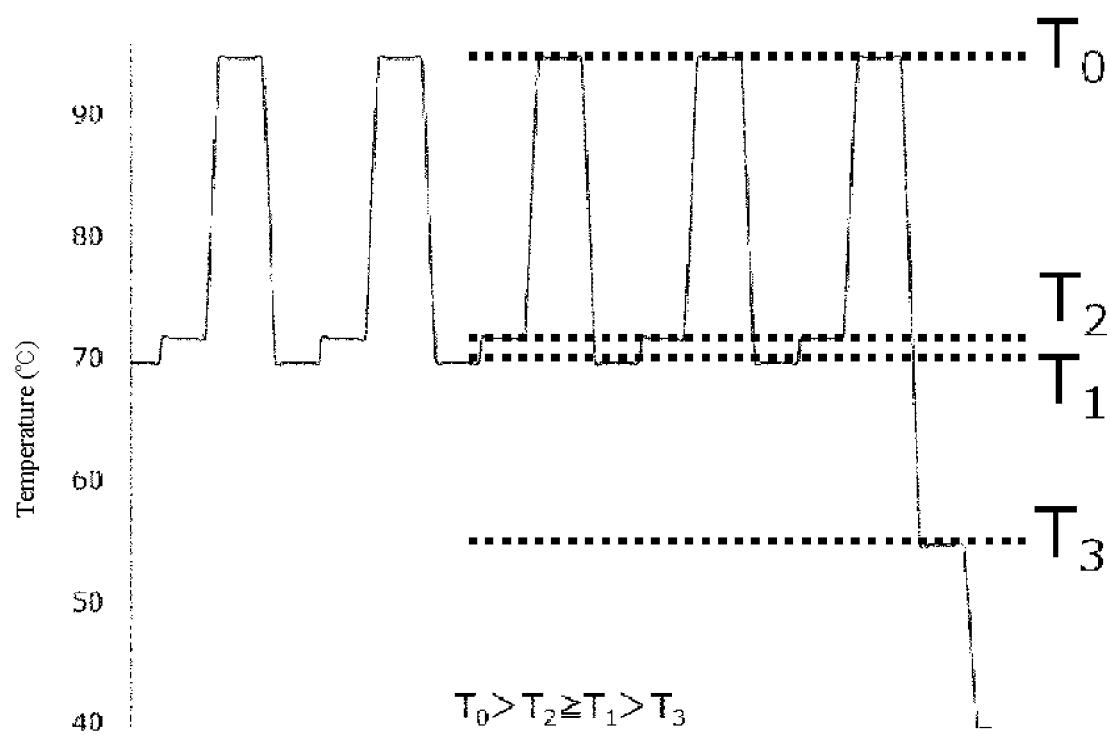
FIG. 21 is a enlarged view showing how temperature in the present invention changes.
Figure 22:
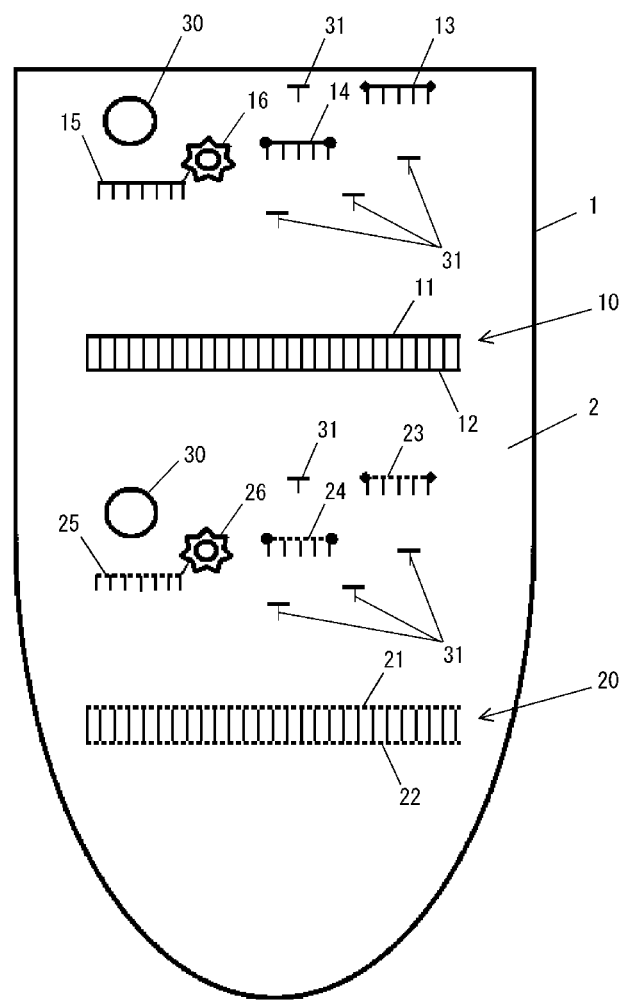
FIG. 22 is an explanatory view showing components of mixed solution in Embodiment 1 of the present invention.
Figure 23A:
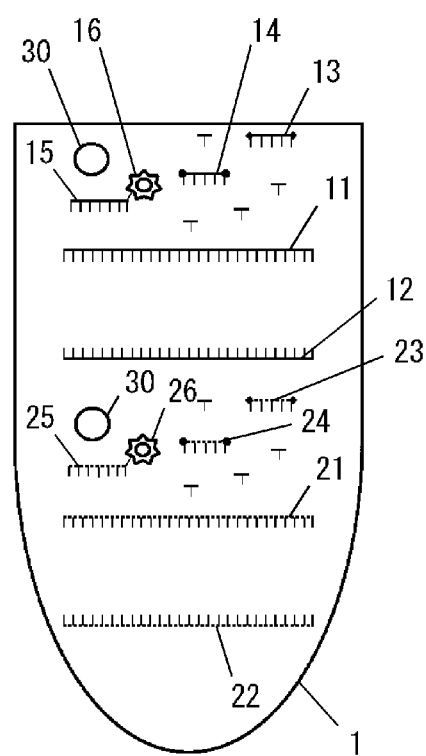
FIG. 23 (a) is an explanatory view of a denaturation step in Embodiment 1 of the present invention.
Figure 23B:
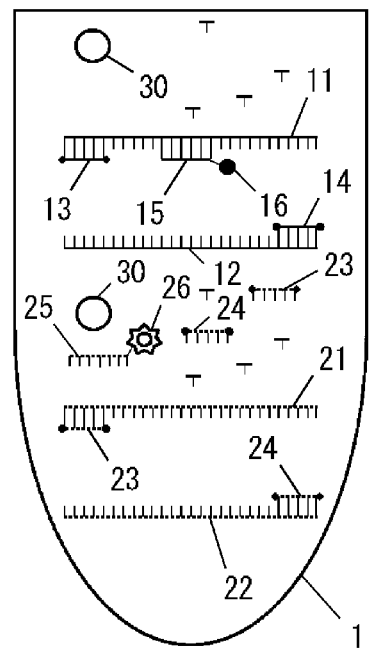
Figure 23C:
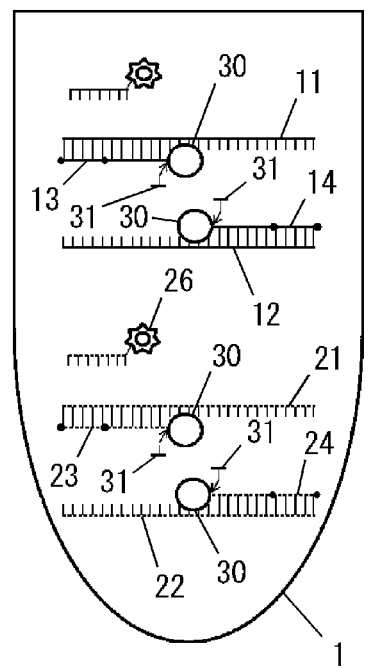
Figure 23D:
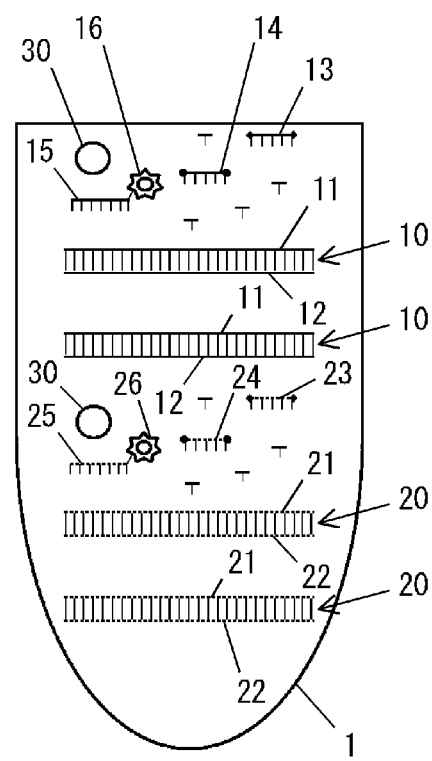
Figure 24A:
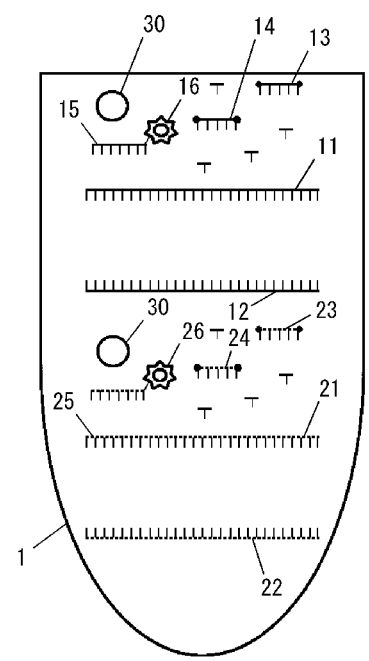
FIG. 24 (a) is an explanatory view of a denaturation step in Embodiment 1 of the present invention.
Figure 24B:
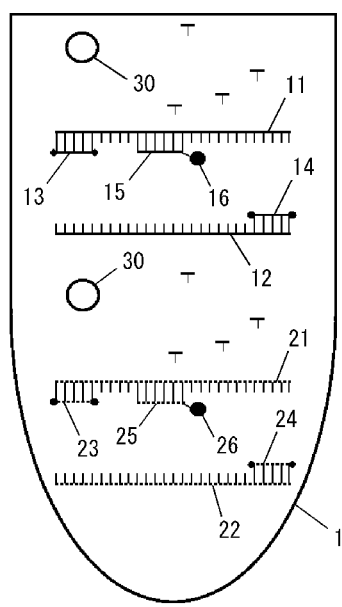

1: Vessel
2: Solution
10: First target nucleic acid
13: F first target's primer
14: R first target's primer
15: First target's probe
16: First labeling substance
20: Second target nucleic acid
23: F second target's primer
24: R second target's primer
25: Second target's probe
26: Second labeling substance
30: DNA polymerase
31: Deoxyribonucleoside triphoshate
T0: Denaturation temperature
T1: Annealing temperature
T2: Elongation temperature
T3: Second target detection temperature

What is claimed is:

1. A detection method, comprising:

performing, including measuring: a fluorescence intensity value in an elongation step of a first target nucleic acid detection step; a fluorescence intensity value in a denaturation step of the first target nucleic acid detection step; a fluorescence intensity value in an elongation step of a first and second target nucleic acid detection step; a fluorescence intensity value in a denaturation step of the first and second target nucleic acid detection step; calculation in accordance with a plurality of formulas for every specific cycle and/or every cycle during amplification reaction; and using a kit for detecting multiple target nucleic acids including a first target nucleic acid and a second target nucleic acid differing from each other, the kit for detecting the multiple target nucleic acids comprises solution, wherein T0 is defined as denaturation temperature; T1 is defined as annealing temperature; T2 is defined as elongation temperature; and T3 is defined as second target detection temperature;

the solution being capable of containing the first target nucleic acid and the second target nucleic acid therein, at the denaturation temperature T0, first double-stranded hydrogen bond of the first target nucleic acid being cut off to be dissociated into first two single strands, second double-stranded hydrogen bond of the second target nucleic acid being cut off to be dissociated into second two single strands, respectively;

the solution further contains therein:

a first target's primer at the annealing temperature T1 specifically bonding with either of the first two single strands into which the first target nucleic acid has been dissociated;

a second target's primer at the annealing temperature T1 specifically bonding with either of the second two single strands into which the second target nucleic acid has been dissociated;

a first target's probe at the annealing temperature T1 specifically bonding with either of the first two single strands into which the first target nucleic acid has been dissociated, the first target's probe including a first labeling substance changing first fluorescent signals thereof when the first target's probe specifically bonds with either of the first two single strands;

DNA polymerase;

deoxyribonucleoside triphoshate at the elongation temperature T2 bonding by action of the DNA polymerase with both of the first two single strands into which the first target nucleic acid has been dissociated and the second two single strands into which the second target nucleic acid has been dissociated;

a second target's probe at the annealing temperature T1 bonding with neither the first two single strands into which the first target nucleic acid has been dissociated nor the second two single strands into which the second target nucleic acid has been dissociated, the second target's probe at the second target detection temperature T3 bonding with the second two single strands into which the second target nucleic acid has been dissociated, the second target's probe including a second labeling substance changing second fluorescent signals thereof when the second target's probe specifically bonds with either of the second two single strands;

wherein the plurality of formulas include:

$$f1[n] = fhyb.1[n]/fden.1[n];\quad\text{(Formula 1)}$$

$$f2[n] = fhyb.2[n]/fden.2[n];\text{ and}\quad\text{(Formula 1')}$$

$$Fr[n] = (a-f2[n])/(a-f1[n]),\quad\text{(Formula 2)}$$

wherein:

$f1[n]$ is a first fluorescence intensity value calculated in accordance with the Formula 1 in a first target nucleic acid detection step in an n-th cycle;

$fhyb.1[n]$ is a second fluorescence intensity value in an elongation step of the first target nucleic acid detection step in the n-th cycle;

$fden.1[n]$ is a third fluorescence intensity value in a denaturation step of the first target nucleic acid detection step in the n-th cycle;

$f2[n]$ is a fourth fluorescence intensity value calculated in accordance with the Formula 1' in a first and second target nucleic acid detection step in the n-th cycle;

$fhyb.2[n]$ is a fifth fluorescence intensity value in an elongation step of the first and second target nucleic acid detection step in the n-th cycle;

$fden.2[n]$ is a sixth fluorescence intensity value in a denaturation step of the first and second target nucleic acid detection step in the n-th cycle;

"a" is a fixed number making Fr not to be zero or less; and

Fr [n] is a first calculated value for detecting the second target nucleic acid.

2. The detection method as defined in claim 1, wherein:

T0 through T3 being set up such that a condition of T0>T2>=T1>T3 is satisfied; and the kit for detecting the multiple target nucleic acids comprises solution;

T0 is defined as denaturation temperature; T1 is defined as annealing temperature; T2 is defined as elongation temperature; and T3 is defined as second target detection temperature, T0 through T3 being set up such that a condition of T0>T2>=T1>T3 is satisfied;

the solution being capable of containing the first target nucleic acid and the second target nucleic acid therein, at the denaturation temperature T0, first double-stranded hydrogen bond of the first target nucleic acid being cut off to be dissociate into first two single strands, second double-stranded hydrogen bond of the second target nucleic acid being cut off to be dissociate into second two single strands, respectively;

the solution further contains therein:

a first target's primer at the annealing temperature T1 specifically bonding with either of the first two single strands into which the first target nucleic acid has been dissociated;

a second target's primer at the annealing temperature T1 specifically bonding with either of the second two single strands into which the second target nucleic acid has been dissociated;

a first target's probe at the annealing temperature T1 specifically bonding with either of the first two single strands into which the first target nucleic acid has been dissociated, the first target's probe including a first labeling substance changing first fluorescent signals thereof when the first target's probe specifically bonds with either of the first two single strands;

DNA polymerase;

deoxyribonucleoside triphoshate at the elongation temperature T2 bonding by action of the DNA polymerase with both of the first two single strands into which the first target nucleic acid has been dissociated and the second two single strands into which the second target nucleic acid has been dissociated;

a second target's probe at the annealing temperature T1 bonding with neither the first two single strands into which the first target nucleic acid has been dissociated nor the second two single strands into which the second target nucleic acid has been dissociated, the second target's probe at the second target detection temperature T3 bonding with the second two single strands into which the second target nucleic acid has been dissociated, the second target's probe including a second labeling substance changing second fluorescent signals thereof when the second target's probe specifically bonds with either of the second two single strands; and the first labeling substance and the second labeling substance are identical to each other so that the first fluorescent signals caused by the first labeling substance and the second fluorescent signals caused by the second labeling substance are also identical to each other.

3. The detection method defined in claim 2, further comprising:

performing further calculation in accordance with further formulas, wherein the further formulas include:

$$F1[n] = f1[n]/f1[X];\quad\text{(Formula 3)}$$

$$F2[n] = f2[n]/f2[X];\text{ and}\quad\text{(Formula 3')}$$

$$Fr'[n] = (a-F2[n])/(a-F1[n]),\quad\text{(Formula 2')}$$

wherein:

$f1[X]$ is a seventh fluorescence intensity value in an X cycle;

the seventh fluorescence intensity $f1[X]$ is stable in the X cycle;

the multiple target nucleic acids have not been amplified yet until the X cycle;

the seventh fluorescence intensity $f1[X]$ is used as a first criterion in change of fluorescence intensity values in the first target nucleic acid detection step;

$f2[X]$ is an eighth fluorescence intensity value in the X cycle;

the eighth fluorescence intensity f2[X] is stable;
the multiple target nucleic acids have not been amplified yet until the X cycle;
the eighth fluorescence intensity f2 [X] being used as a second criterion in change of fluorescence intensity values in the first and second target nucleic acid detection step;
F1[n] is a first relative value in the n-th cycle when assuming a fluorescence intensity value obtained in accordance with the Formula 3 in the X cycle as "1";
F2[n] is a second relative value in the n-th cycle when assuming a fluorescence intensity value obtained in accordance with the Formula 3' in the X cycle as "1"; and
Fr' [n] is a second calculated value for detecting the second target nucleic acid.

4. A detection method, comprising:
performing, including measuring: a fluorescence intensity value in an elongation step of a first target nucleic acid detection step; a fluorescence intensity value in a denaturation step of the first target nucleic acid detection step; a fluorescence intensity value in an elongation step of a first and second target nucleic acid detection step; a fluorescence intensity value in a denaturation step of the first and second target nucleic acid detection step; calculation in accordance with a plurality of formulas with respect to melting curve analysis for every specific cycle and/or every cycle during amplification reaction; and
using a kit for detecting multiple target nucleic acids,
the kit for detecting the multiple target nucleic acids comprises solution, wherein T0 is defined as denaturation temperature; T1 is defined as annealing temperature; T2 is defined as elongation temperature; and T3 is defined as second target detection temperature;
the solution being capable of containing the first target nucleic acid and the second target nucleic acid therein, at the denaturation temperature T0, first double-stranded hydrogen bond of the first target nucleic acid being cut off to be dissociated into first two single strands, second double-stranded hydrogen bond of the second target nucleic acid being cut off to be dissociated into second two single strands, respectively;
the solution further contains therein:
a first target's primer at the annealing temperature T1 specifically bonding with either of the first two single strands into which the first target nucleic acid has been dissociated;
a second target's primer at the annealing temperature T1 specifically bonding with either of the second two single strands into which the second target nucleic acid has been dissociated;
a first target's probe at the annealing temperature T1 specifically bonding with either of the first two single strands into which the first target nucleic acid has been dissociated, the first target's probe including a first labeling substance changing first fluorescent signals thereof when the first target's probe specifically bonds with either of the first two single strands;

DNA polymerase;
deoxyribonucleoside triphoshate at the elongation temperature T2 bonding by action of the DNA polymerase with both of the first two single strands into which the first target nucleic acid has been dissociated and the second two single strands into which the second target nucleic acid has been dissociated;
a second target's probe at the annealing temperature T1 bonding with neither the first two single strands into which the first target nucleic acid has been dissociated nor the second two single strands into which the second target nucleic acid has been dissociated, the second target's probe at the second target detection temperature T3 bonding with the second two single strands into which the second target nucleic acid has been dissociated, the second target's probe including a second labeling substance changing second fluorescent signals thereof when the second target's probe specifically bonds with either of the second two single strands;
wherein the plurality of formulas include:

$f1m = fhyb.1m/fden.1m;$ (Formula 4)

$f2m = fhyb.2m/fden.2m;$ and (Formula 4')

$Frm = (a-f2m)/(a-f1m),$ (Formula 5)

wherein:
f1m is a first fluorescence intensity value calculated with respect to a melting curve in accordance with the Formula 4 in a first target nucleic acid detection step;
fhyb.1m is a second fluorescence intensity value at first probe for first target hybridization temperature with respect to the melting curve;
fden.1m is a third fluorescence intensity value at first probe for first target dissociation temperature with respect to the melting curve;
f2m is a fourth fluorescence intensity value calculated in accordance with the Formula 4' with respect to the melting curve in a first and second target nucleic acid detection step;
fhyb.2m is a fifth fluorescence intensity value at second probe for second target hybridization temperature with respect to the melting curve;
fden.2m is a sixth fluorescence intensity value at second probe for second target dissociation temperature with respect to the melting curve and is identical to fden.1m;
"a" is a fixed number making Frm to not be zero or less; and
Frm is a third calculated value for detecting the second target nucleic acid.

5. The detection method as defined in claim 1, wherein the fluorescent signals are shown by at least one of:
emitting light when annealing occurs; and
quenching light when annealing occurs.

6. The detection method as defined in claim 1, wherein a pair of the first target nucleic acid and the second target nucleic acid is at least one of:
a wild type sequence of a *Mycoplasma* 23S rRNA gene and a sequence with drug resistance variation of a *Mycoplasma* 23S rRNA gene; and
a *Chlamydia* endogeneous plasmid gene and a *Nisseria gonorrhoeae* cytosine methyltransferase CMT gene.

* * * * *